US012667707B2

(12) United States Patent
Stanton et al.

(10) Patent No.: US 12,667,707 B2
(45) Date of Patent: Jun. 30, 2026

(54) UNIVERSAL THREAD FLUID CONTAINER ENCLOSURE SYSTEMS

(71) Applicant: Boston Scientific Scimed, Inc., Maple Grove, MN (US)

(72) Inventors: Larry Edward Stanton, Burlington, MA (US); Matthew LaPlaca, Franklin, MA (US); Ryan Vincent William Pollock, Leominster, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1196 days.

(21) Appl. No.: 17/480,871

(22) Filed: Sep. 21, 2021

(65) Prior Publication Data

US 2022/0095906 A1 Mar. 31, 2022

Related U.S. Application Data

(60) Provisional application No. 63/084,292, filed on Sep. 28, 2020, provisional application No. 63/084,284, (Continued)

(51) Int. Cl.
*A61M 39/14* (2006.01)
*A61B 1/00* (2006.01)
(Continued)

(52) U.S. Cl.
CPC ......... *A61M 39/14* (2013.01); *A61B 1/00121* (2013.01); *A61B 1/00128* (2013.01); (Continued)

(58) Field of Classification Search
CPC .......... A61J 1/14; A61J 1/1418; A61J 1/1481; A61M 39/14; A61M 39/10; (Continued)

(56) References Cited

U.S. PATENT DOCUMENTS

| | | | | |
|---|---|---|---|---|
| 2,812,117 | A | * | 11/1957 | Butkus ................. A61J 1/1487 |
| | | | | 222/189.09 |
| 3,467,270 | A | * | 9/1969 | Edsell ................... A61J 1/1418 |
| | | | | 215/311 |

(Continued)

FOREIGN PATENT DOCUMENTS

| | | |
|---|---|---|
| CN | 210330526 U | 4/2020 |
| EP | 0747293 A1 | 12/1996 |
| EP | 1897816 A1 | 3/2008 |

OTHER PUBLICATIONS

International Search Report and Written Opinion dated Feb. 10, 2022 for International Application No. PCT/US2021/051308.

(Continued)

*Primary Examiner* — Bhisma Mehta
*Assistant Examiner* — Mark A Igel
(74) *Attorney, Agent, or Firm* — Seager, Tufte & Wickhem, LLP

(57) ABSTRACT

Various embodiments are generally directed to fluid container enclosure systems that couple with a fluid container and enable different systems, such as endoscopic systems, to access the contents of the fluid container, such as via a tubing set. The enclosure systems are configured to fit a wide range of fluid container necks, ports, or other openings, including various opening dimensions, thread finishes, and/ or thread dimensions. In one embodiments, an enclosure system may include a cap having multiple carriages arranged therein. For example, a primary carriage may be arranged within the cap to engage with larger-dimensioned bottles. A secondary carriage may be arranged to float within the primary carriage to engage smaller-dimensioned bottles that bypass the primary carriage. Other embodiments are described.

14 Claims, 18 Drawing Sheets

Related U.S. Application Data filed on Sep. 28, 2020, provisional application No. 63/084,297, filed on Sep. 28, 2020, provisional application No. 63/084,274, filed on Sep. 28, 2020.

(51) Int. Cl.

| | |
|---|---|
| *A61B 1/005* | (2006.01) |
| *A61B 1/015* | (2006.01) |
| *A61J 1/14* | (2023.01) |
| *A61M 39/10* | (2006.01) |

(52) U.S. Cl.
CPC ........ *A61B 1/00137* (2013.01); *A61B 1/0058* (2013.01); *A61B 1/015* (2013.01); *A61J 1/1418* (2015.05); *A61J 1/1481* (2015.05); *A61M 39/10* (2013.01); *A61M 2039/1077* (2013.01)

(58) Field of Classification Search
CPC ....... A61M 2039/1077; A61B 1/00121; A61B 1/00128; A61B 1/00137; A61B 1/0058; A61B 1/015
See application file for complete search history.

(56) References Cited

U.S. PATENT DOCUMENTS

| | | | | |
|---|---|---|---|---|
| 3,893,582 | A | | 7/1975 | Kowalik |
| 3,923,062 | A | * | 12/1975 | St. Amand ............ A61J 1/1418 |
| | | | | 215/246 |
| 4,015,400 | A | * | 4/1977 | Choksi .................. A61J 1/1418 |
| | | | | 53/492 |
| 4,365,722 | A | * | 12/1982 | Kramer ..................... A61J 7/04 |
| | | | | 206/534 |
| 5,513,763 | A | * | 5/1996 | Adams .............. B65D 41/0471 |
| | | | | 141/354 |
| 5,738,663 | A | * | 4/1998 | Lopez ................... A61M 39/10 |
| | | | | 604/249 |
| 5,857,579 | A | | 1/1999 | Finneran |
| 6,341,706 | B1 | * | 1/2002 | Neuner ................. B65D 51/32 |
| | | | | 222/570 |
| 6,875,204 | B1 | * | 4/2005 | Hopkins .............. A61J 1/1418 |
| | | | | 604/416 |
| 7,857,172 | B2 | * | 12/2010 | Harvey ................ B05B 11/105 |
| | | | | 222/321.1 |
| 8,100,879 | B2 | * | 1/2012 | Blank .................... B65D 5/746 |
| | | | | 222/81 |
| 10,006,567 | B2 | * | 6/2018 | Zumbrum ............ B65D 51/002 |
| 10,220,984 | B1 | | 3/2019 | Vigoureux |
| 2002/0173748 | A1 | * | 11/2002 | McConnell .......... A61M 39/04 |
| | | | | 604/533 |
| 2003/0187420 | A1 | * | 10/2003 | Akerlund .............. A61J 1/1406 |
| | | | | 604/408 |
| 2007/0093775 | A1 | * | 4/2007 | Daly ..................... A61J 1/1418 |
| | | | | 604/414 |
| 2007/0129705 | A1 | * | 6/2007 | Trombley, III ....... A61M 39/10 |
| | | | | 604/523 |
| 2009/0264705 | A1 | * | 10/2009 | Cushner ................... A61B 1/12 |
| | | | | 600/158 |
| 2010/0152700 | A1 | * | 6/2010 | Paine .................... A61J 1/1406 |
| | | | | 604/257 |
| 2010/0327010 | A1 | * | 12/2010 | Manera .............. B65D 47/2031 |
| | | | | 141/357 |
| 2012/0277536 | A1 | * | 11/2012 | Kaye ........................ A61B 1/12 |
| | | | | 264/271.1 |
| 2013/0200033 | A1 | * | 8/2013 | Zonana ............. B65D 83/0409 |
| | | | | 215/231 |
| 2014/0316204 | A1 | * | 10/2014 | Ofir .................... A61B 1/00119 |
| | | | | 600/158 |
| 2015/0001261 | A1 | * | 1/2015 | Johnson ................. B67D 3/045 |
| | | | | 53/469 |
| 2016/0031615 | A1 | * | 2/2016 | Miceli ....................... A61J 1/00 |
| | | | | 220/288 |
| 2016/0120756 | A1 | * | 5/2016 | Nazginov ................. A61J 7/04 |
| | | | | 215/230 |
| 2016/0207684 | A1 | * | 7/2016 | Johnson ................. B65D 5/747 |
| 2017/0066571 | A1 | | 3/2017 | Panec et al. |
| 2018/0008812 | A1 | * | 1/2018 | Roxas .................... A61M 1/367 |
| 2019/0023469 | A1 | * | 1/2019 | Bugenske .......... B65D 41/0471 |
| 2019/0092538 | A1 | * | 3/2019 | Johnson .............. B65D 47/121 |
| 2019/0110665 | A1 | * | 4/2019 | Mann ................. A61B 1/00119 |
| 2019/0117046 | A1 | * | 4/2019 | Briggs ................... A61B 1/126 |
| 2019/0193922 | A1 | * | 6/2019 | Poirier ................ B65D 83/049 |
| 2020/0026860 | A1 | | 1/2020 | Aldridge et al. |
| 2020/0206084 | A1 | * | 7/2020 | Tsukanov .................. A61J 1/03 |
| 2022/0105283 | A1 | * | 4/2022 | Litke ..................... A61B 17/34 |
| 2024/0148609 | A1 | * | 5/2024 | Battle ................... A61J 1/1418 |
| 2024/0174412 | A1 | * | 5/2024 | Wellhöfer-Meyer ....................... B65D 41/0442 |

OTHER PUBLICATIONS

European Search Report for European Application No. 24202923.9, dated Dec. 23, 2024. (8 Pages).

Invite to Pay Additional Fees dated Dec. 20, 2021 for International Application No. PCT/US2021/051308.

* cited by examiner

504

503

505

500

502

510

501

507

950

951

960

961

970

971

1

UNIVERSAL THREAD FLUID CONTAINER ENCLOSURE SYSTEMS

PRIORITY

The present application claims the benefit of priority under 35 U.S.C. § 119 to U.S. Provisional Application Ser. Nos. 63/084,274, 63/084,284, 63/084,292, and 63/084,297, each filed Sep. 28, 2020, the disclosures of which are incorporated herein by reference in their entirety.

FIELD

The present disclosure relates generally to enclosures for fluid containers. In particular, the present disclosure relates to universal fluid container enclosures for endoscopic systems.

BACKGROUND

Endoscopy procedures that use typical endoscopes for both therapeutic and diagnostic cases usually have some common functionalities available to an operator. One of the common functionalities includes the ability to insufflate a patient by passing a fluid, such as air or carbon dioxide, through the endoscope in a controlled manner into a target luminal space. Another of the common functionalities includes the ability to flush water across the imaging lens to clear the field of view. Yet another of the common functionalities includes the ability to irrigate the lumen to clean surfaces and aid in flushing/suctioning debris during a procedure. Oftentimes, these common functionalities, among others, are facilitated by one or more fluid containers and/or fluid sources. For example, an air pump or carbon dioxide source for insufflation, a water bottle for lens cleaning, and/or a sterile water bottle for irrigation. In some cases, a hybrid tubing set may be used for both lens cleaning and irrigation from a sterile water bottle. The one or more fluid containers and/or sources, each potentially with a different size and/or configuration, must be attached to the tubing set of the endoscope. It is with all of the above considerations in mind that the improvements of the present disclosure may be useful.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In one embodiment, the present disclosure relates to an enclosure system for a fluid container. For example, an enclosure system for enclosing a plurality of types of fluid containers may include a cap comprising an internal cavity, a primary carriage coupled to the cap within the internal cap cavity, the primary carriage comprising a set of primary internal threads configured to engage larger-dimensioned port threads of a larger-dimensioned port of one of the plurality of types of fluid containers, and a secondary carriage arranged within an internal primary cavity of the primary carriage, the secondary carriage comprising secondary internal threads configured to engage smaller-dimensioned port threads of a smaller-dimensioned port of one of the plurality of types of fluid containers.

In some embodiments of the enclosure system, the enclosure system may include at least one tube of an internal tube set to extend through the cap to access a fluid arranged with the fluid container.

In various embodiments of the enclosure system, the enclosure system may include a spring configured to bias the secondary carriage toward the primary carriage.

In some embodiments of the enclosure system, the enclosure system may include a sealing element arranged on a bottom internal surface of the cap, and the sealing element may be configured to engage a top surface of an installed port to form a seal between the cap and the installed port.

In various embodiments of the enclosure system, the cap may include a set of internal cap threads arranged on an inner wall of the internal cavity, and the primary carriage may include a set of primary external threads configured to engage the internal cap threads to hold the primary carriage within the cap.

In exemplary embodiments of the enclosure system, the cap may include a shoulder arranged on an inner wall of the internal cavity, and the primary carriage may be configured to be snap-fit via the shoulder to hold the primary carriage within the cap.

In various embodiments of the enclosure system, a difference in an outer dimension of threads of the larger-dimensioned port and the smaller-dimensioned port may be about 2 mm to about 4 mm.

In some embodiments of the enclosure system, the cap may be configured to enclose ports having an outer dimension of threads of about 30 mm to about 40 mm.

In various embodiments of the enclosure system, the primary carriage may include at least one guiding slot arranged in an internal surface thereof and the secondary carriage may include at least one guiding boss arranged on an external surface thereof, the at least one guiding boss may be configured to be seated within the at least one guiding slot to prevent rotation of the secondary carriage within the cap.

In one embodiment, the present disclosure relates to an enclosure system for a fluid container. For example, an enclosure system for enclosing a plurality of types of fluid containers may include a cap component that includes a skirt having a plurality of internal threads arranged on an internal surface thereof to engage port threads of a port of the plurality of types of fluid containers, and a biasing component coupled to a portion of the skirt to bias the skirt inward. The skirt may be configured to expand outward against biasing of the biasing component responsive to internal pressure of the port on the internal surface as the cap component is pushed down on the port to increase an inner diameter of the skirt to allow the plurality of internal threads to engage port threads having different dimensions.

In some embodiments of the enclosure system, the skirt may include a plurality of legs arranged between slots formed in the cap component.

In various embodiments of the enclosure system, the biasing component may include a ring arranged within a groove extending circumferentially around skirt.

In some embodiments of the enclosure system, the different dimensions may include a difference of an outer dimension of threads of about 2 mm to about 4 mm.

In one embodiment, the present disclosure relates to an enclosure system for a fluid container. For example, an enclosure system for enclosing a plurality of types of fluid containers may include a cap comprising internal cap threads arranged on an internal surface and at least one insert comprising external insert threads configured to engage the internal cap threads to hold the insert within cap and internal port threads configured to receive threads of a port of one of the plurality of types of fluid containers.

In some embodiments of the enclosure system, the cap may be to receive inserts configured to be installed on ports having a difference of dimension of threads of about 2 mm to about 4 mm.

In one embodiment, the present disclosure relates to an apparatus. For example, an apparatus for performing an endoscopic procedure may include a fluid container and an enclosure system for enclosing the fluid container. The enclosure system configured to be installed on a plurality of types of fluid containers. The enclosure system may include a cap comprising an internal cavity, a primary carriage coupled to the cap within the internal cap cavity, the primary carriage comprising a set of primary internal threads configured to engage larger-dimensioned port threads of a larger-dimensioned port of one of the plurality of types of fluid containers, and a secondary carriage arranged within an internal primary cavity of the primary carriage, the secondary carriage comprising secondary internal threads configured to engage smaller-dimensioned port threads of a smaller-dimensioned port of one of the plurality of types of fluid containers.

In some embodiments of the apparatus, the apparatus may further include a spring configured to bias the secondary carriage toward the primary carriage.

In various embodiments of the apparatus, the apparatus may further include a sealing element arranged on a bottom internal surface of the cap, the sealing element configured to engage a top surface of an installed port to form a seal between the cap and the installed port.

In some embodiments of the apparatus, a difference in an outer dimension of threads of the larger-dimensioned port and the smaller-dimensioned port may be about 2 mm to about 4 mm.

In exemplary embodiments of the apparatus, the cap may be configured to enclose ports having an outer dimension of threads of about 30 mm to about 40 mm.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters. For purposes of clarity and simplicity, not every element is labeled in every figure, nor is every element of each embodiment shown where illustration is not necessary to allow those of ordinary skill in the art to understand the disclosure.

The Detailed Description will be better understood in conjunction with the accompanying drawings, wherein like reference characters represent like elements, as follows.

DETAILED DESCRIPTION

Figure 1:
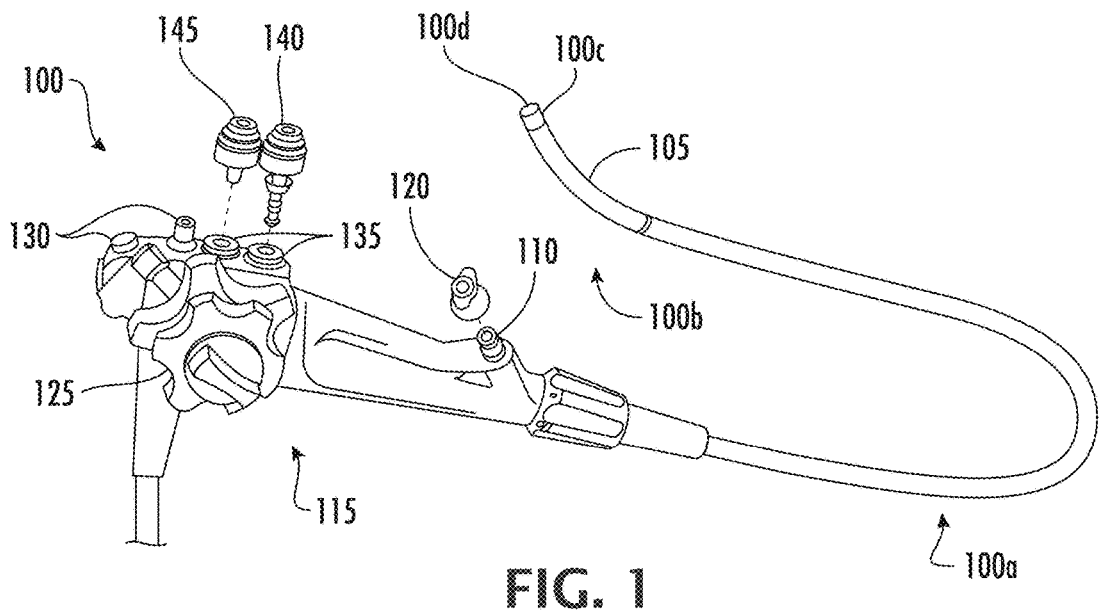
FIG. 1 depicts components of an endoscope.

The following Detailed Description should be read with reference to the drawings, which depict illustrative embodiments. It is to be understood that the present disclosure is not limited to the particular embodiments described, as such may vary. All apparatuses and systems and methods discussed herein are examples of apparatuses and/or systems and/or methods implemented in accordance with one or more principles of the present disclosure. Each example of an embodiment is provided by way of explanation and is not the only way to implement these principles but are merely examples. Thus, references to elements or structures or features in the drawings must be appreciated as references to examples of embodiments of the present disclosure, and should not be understood as limiting the present disclosure to the specific elements, structures, or features illustrated. Other examples of manners of implementing the disclosed principles will occur to a person of ordinary skill in the art upon reading the present disclosure. It will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

The described technologies are generally directed to fluid container enclosures configured to be coupled to a fluid container, for example, to seal the fluid container while enabling access to the contents of the fluid container, such as from an endoscopic system via a tubing set. A fluid container may be or may include a bottle or reservoir (see for example, reservoir 270). The fluid container enclosures may be configured as a cap, lid, or other enclosure component capable of sealing a fluid container. In some embodiments, the fluid container enclosures may include openings, lumens, holes, or other elements capable of allowing tubing access to the contents of the fluid container while maintaining a seal. Fluid container enclosures according to some embodiments are configured to operate with fluid containers of various properties, such as size, port or neck configuration, thread configuration, and/or the like. Accordingly, fluid container enclosures according to some embodiments may operate as universal enclosures that are able to be used with a wide array of fluid container configurations, including fluid containers made by different manufacturers and fluid containers having different shapes, sizes, neck configurations, thread configurations, and/or the like.

Some challenges in coupling with a fluid container and gaining access to the contents of the fluid container may include having a fluid container enclosure that is compatible with the fluid container. For example, a fluid container enclosure may include a screw cap with one or more tubes extending therethrough. In such examples, the screw cap may couple to corresponding threads on a neck of the fluid container with the one or more tubes extending therethrough enabling the endoscopic system to access the contents of the fluid container. However, there are many different types of fluid container manufacturers that offer different fluid container designs. Further, manufacturers may offer different fluid container designs and/or periodically change or update fluid container designs. For instance, manufacturers may offer designs with different thread patterns or neck sizes around the world based on regional preferences or demands. This presents a challenge for manufacturers of tubing sets by requiring them to offer multiple products with customized fluid container enclosures for each design. Further, product acquisition and stocking by health care facilities is complicated by necessitating that they ensure that tubing sets have a fluid container enclosure that is compatible with an available fluid container.

In addition, irrigation and lens cleaning may be employed in all endoscopic procedures by connecting a tubing set to a reservoir fluid container, such as a water or irrigation bottle. Some bottles are re-usable and require cleaning and to prevent patient infection, while some bottles are single use sterile containers. Bottle thread designs vary from manufacturer to manufacturer, requiring various configurations of conventional caps to fit the many models of bottle. Accordingly, there is a desire for a cap configuration capable of attaching to the many different types of bottles with minimal configuration changes. Moreover, some endoscopic procedures choose to use alternative methods of insufflation and forward-facing irrigation, which require alternative connections to the 1-day use caps in conjunction with specified sterile water bottles. This increases the number of potential configurations required and can result in the wrong type in the operation room, thereby increasing procedure times. Accordingly, there is a also a need for a fluid container cap that incorporates both insufflation and irrigation options into one cap and tubing set.

Accordingly, various embodiments of the present disclosure include fluid container enclosures that widen the scope of compatibility to a variety of different fluid container designs and/or functionality types, such as insufflation and irrigation. In many embodiments, one or more fluid container enclosures of the present disclosure may provide an efficient, safe, and effective way to couple with and gain access to the contents of a multitude of fluid container designs. Enabling fluid container enclosures to be compatible with different fluid container designs allows manufacturers of tubing sets to offer products that are more adaptable. Further, enabling fluid container enclosures to be compatible with different fluid container designs can simplify product acquisition and stocking by health care facilities.

For example, enclosure systems according to some embodiments may be used with a wide variety of fluid container port, opening, or neck dimensions, such as an opening diameter and/or thread configuration (for instance, Glass Packaging Institute (GPI) thread finish, "H" dimension, thread distance, thread dimensions, and/or the like), thread pitch, outer diameter (OD) of port or neck (OD port), OD of threads (OD thread), thread width, and/or the like. In addition, enclosure systems according to some embodiments may be used on fluid containers made by various manufacturers.

For example, in some embodiments, an enclosure system may include a single cap that is capable of being installed on containers having an opening size (e.g., neck OD, not including threads) of about 10 mm, about 20 mm, about 30 mm, about 40 cm mm about 50 mm, about 100 mm, about 200 mm, and any value or range between any two of these values (including endpoints). In some embodiments, an enclosure system may include a single cap that is capable of being installed on containers having an opening size (e.g., neck OD, not including threads) of about 30 mm, about 30.4 mm, about 31 mm, about 32 mm, about 32.2 mm to about 32.9 mm, about 33 mm, about 33.6 mm, about 34 mm, about 35 mm, about 40 mm, and any value or range between any two of these values (including endpoints).

In some embodiments, an enclosure system may include a single cap that is capable of being installed on containers having a total opening size (e.g., neck OD including threads) of about 10 mm, about 20 mm, about 30 mm, about 40 cm mm about 50 mm, about 100 mm, about 200 mm, and any value or range between any two of these values (including endpoints). In some embodiments, an enclosure system may include a single cap that is capable of being installed on containers having a total opening size (e.g., neck OD including threads) of about 30 mm, about 31 mm, about 32 mm, about 33 mm, about 33.2 mm, about 34 mm, about 35 mm, about 35.75 mm, about 36 mm, about 36.26 mm, about 40 mm, and any value or range between any two of these values (including endpoints).

In some embodiments, an enclosure system may include a single cap that is capable of being installed on containers having a thread width of about 0.5 mm, about 1 mm, about 2 mm, about 3 mm, about 4 mm, about 5 mm, about 10 mm, and any value or range between any two of these values (including endpoints). In some embodiments, an enclosure system may include a single cap that is capable of being installed on containers having a thread width of about 1 mm, about 1.83 mm, about 2 mm, about 2.4 mm, about 2.66 mm, about 3 mm, and any value or range between any two of these values (including endpoints).

In some embodiments, an enclosure system may include a single cap that is capable of being installed on containers having a thread pitch of about 1 mm, about 2 mm, about 3 mm, about 4 mm, about 5 mm, about 6 mm, about 7 mm, about 8 mm, about 9 mm, about 10 mm, and any value or range between any two of these values (including endpoints). In some embodiments, an enclosure system may include a single cap that is capable of being installed on containers having a thread pitch of about 3 mm, about 3.94 mm, about 4 mm, about 4.23 mm, about 4.25 mm, about 5 mm, and any value or range between any two of these values (including endpoints).

In some embodiments, an enclosure system may include a single cap that is capable of being installed on a fluid container having a GPI thread finish of 350, 400, 410, 415, 425, 430, 450, and any value or range between any two of these values (including endpoints).

In various embodiments, an enclosure system may include a single cap that is capable of being installed on different types of fluid container ports or necks. For example, a cap of an enclosure system according to some embodiments may be installed on (and form a seal with) fluid container ports with different dimensions. In some embodiments, an enclosure system may include a single cap that is capable of being installed on a plurality of fluid container ports having a OD thread difference ($\Delta$ OD thread) (i.e., the difference between an OD thread of the smallest OD thread port and the largest OD thread port) of about 0.25 mm, about 0.5 mm, about 1 mm, about 1.5 mm, about 2 mm, about 3 mm, about 4 mm, about 5 mm, about 10 mm, and any value or range between any two of these values (including endpoints). In various embodiments, an enclosure system may include a single cap that is capable of being installed on a plurality of fluid container ports having a OD port difference ($\Delta$ OD port) (i.e., the difference between an OD port of the port with the smallest OD port and the port with the largest OD port) of about 0.25 mm, about 0.5 mm, about 1 mm, about 1.5 mm, about 2 mm, about 3 mm, about 4 mm, about 5 mm, about 10 mm, and any value or range between any two of these values (including endpoints).

The described embodiments may provide additional advantages that would be known to those of skill in the art.

It may be understood that the disclosure included herein is exemplary and explanatory only and is not restrictive. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Although endoscopes and endoscopic systems are referenced herein, reference to endoscopes, endoscopic systems, or endoscopy should not be construed as limiting the possible applications of the disclosed aspects. For example, the disclosed aspects may be used in conjunction with duodenoscopes, bronchoscopes, ureteroscopes, colonoscopes, catheters, diagnostic or therapeutic tools or devices, or other types of medical devices or systems.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

Figure 2:
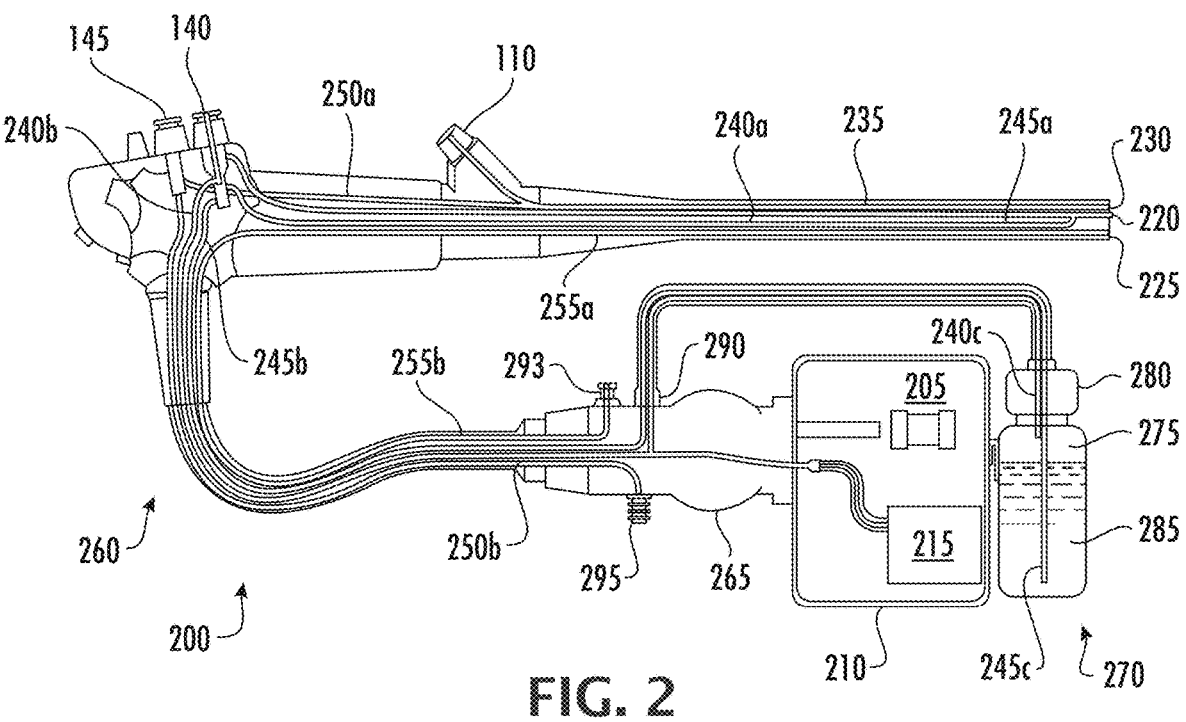
FIG. 2 depicts components of an endoscope system.

With reference to FIGS. 1-2, an exemplary endoscope 100 and system 200 is depicted that may comprise an elongated shaft 100a that is inserted into a patient. A light source 205 feeds illumination light to a distal portion 100b of the endoscope 100, which may house an imager (e.g., CCD or CMOS imager) (not shown). The light source 205 (e.g., lamp) is housed in a video processing unit 210 that processes signals that are input from the imager and outputs processed video signals to a video monitor (not shown) for viewing. The video processing unit 210 also serves as a component of an air/water feed circuit by housing a pressurizing pump 215, such as an air feed pump, in the unit.

The endoscope shaft 100a may include a distal tip 100c provided at the distal portion 100b of the shaft 100a and a flexible bending portion 105 proximal to the distal tip 100c. The flexible bending portion 105 may include an articulation joint (not shown) to assist with steering the distal tip 100c. On an end face 100d of the distal tip of the endoscope 100 is a gas/lens wash nozzle 220 for supplying gas to insufflate the interior of the patient at the treatment area and for supplying water to wash a lens covering the imager. An irrigation opening 225 in the end face 100d supplies irrigation fluid to the treatment area of the patient. Illumination windows (not shown) that convey illumination light to the treatment area, and an opening 230 to a working channel 235 extending along the shaft 100a for passing tools to the treatment area, also may be included on the face 100d of the distal tip 100c. The working channel 235 extends along the shaft 100a to a proximal channel opening 110 positioned distal to an operating handle 115 of the endoscope 100. A biopsy valve 120 may be utilized to seal the channel opening 110 against unwanted fluid egress.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115. In addition, the handle is provided with dual valve wells 135 that receive a gas/water valve 140 for operating an insufflating gas and lens water feed operation. A gas supply line 240a and a lens wash supply line 245a run distally from the gas/water valve 140 along the shaft 100a and converge at the distal tip 100c proximal to the gas/wash nozzle 220 (FIG. 2). The other valve well 135 receives a suction valve 145 for operating a suction operation. A suction supply line 250a runs distally from the suction valve 145 along the shaft 100a to a junction point in fluid communication with the working channel 235 of the endoscope 100.

The operating handle 115 is electrically and fluidly connected to the video processing unit 210, via a flexible umbilical 260 and connector portion 265 extending therebetween. The flexible umbilical 260 has a gas (e.g., air or CO2) feed line 240b, a lens wash feed line 245b, a suction feed line 250b, an irrigation feed line 255b, a light guide (not shown), and an electrical signal cable. The connector portion 265 when plugged into the video processing unit 210 connects the light source 205 in the video processing unit with the light guide. The light guide runs along the umbilical 260 and the length of the endoscope shaft 100a to transmit light to the distal tip 100c of the endoscope 100. The connector portion 265 when plugged into the video processing unit 210 also connects the air pump 215 to the gas feed line 240b in the umbilical 260.

A water reservoir 270 (e.g., water bottle) is fluidly connected to the endoscope 100 through the connector portion 265 and the umbilical 260. A length of gas supply tubing 240c passes from one end positioned in an air gap 275 between the top 280 (e.g., bottle cap or enclosure) of the reservoir 270 and the remaining water 285 in the reservoir to a detachable gas/lens wash connection 290 on the outside of the connector portion 265. The gas feed line 240b from the umbilical 260 branches in the connector portion 265 to fluidly communicate with the gas supply tubing 240c at the detachable gas/lens wash connection 290, as well as the air pump 215. A length of lens wash tubing 245c, with one end positioned at the bottom of the reservoir 270, passes through the top (e.g., a cap or enclosure) 280 of the reservoir 270 to the same detachable connection 290 as the gas supply tubing 240c on the connector portion 265. In other embodiments, the connections may be separate and/or separated from each other. The connector portion 265 also has a detachable irrigation connection 293 for irrigation supply tubing (not shown) running from a source of irrigation water (not shown) to the irrigation feed line 255b in the umbilical 260. In some embodiments, irrigation water is supplied via a pump (e.g., peristaltic pump) from a water source independent (not shown) from the water reservoir 270. In other embodiments, the irrigation supply tubing and lens wash tubing 245c may source water from the same reservoir. The connector portion 265 may also include a detachable suction connection 291 for suction feed line 250b and suction supply line 250a fluidly connecting a vacuum source (e.g., hospital house suction) (not shown) to the umbilical 260 and endoscope 100.

The gas feed line 240b and lens wash feed line 245b are fluidly connected to the valve well 135 for the gas/water valve 140 and configured such that operation of the gas/water valve in the well controls supply of gas or lens wash to the distal tip 100c of the endoscope 100. The suction feed line 250b is fluidly connected to the valve well 135 for the suction valve 145 and configured such that operation of the suction valve in the well controls suction applied to the working channel 235 of the endoscope 100.

Referring to FIG. 2, an exemplary operation of an endoscopic system 200, including an endoscope such as endoscope 100 above, is explained. Air from the air pump 215 in the video processing unit 210 is flowed through the connection portion 265 and branched to the gas/water valve 140 on the operating handle 115 through the gas feed line 240b in the umbilical 260, as well as through the gas supply tubing 240c to the water reservoir 270 via the connection 290 on the connector portion 265. When the gas/water valve 140 is in a neutral position, without the user's finger on the valve, air is allowed to flow out of the valve to atmosphere. In a first position, the user's finger is used to block the vent to atmosphere. Gas is allowed to flow from the valve 140 down the gas supply line 240a and out the distal tip 100c of the endoscope 100 in order to, for example, insufflate the treatment area of the patient. When the gas/water valve 140 is pressed downward to a second position, gas is blocked from exiting the valve, allowing pressure of the air passing from the air pump 215 to rise in the water reservoir 270. Pressurizing the water source forces water out of the lens wash tubing 245c, through the connector portion 265, umbilical 260, through the gas/water valve 140 and down the lens wash supply line 245a, converging with the gas supply line 240a prior to exiting the distal tip 100c of the endoscope 100 via the gas/lens wash nozzle 220. Air pump pressure may be calibrated to provide lens wash water at a relatively low flow rate compared to the supply of irrigation water.

The volume of the flow rate of the lens wash is governed by gas pressure in the water reservoir 270. When gas pressure begins to drop in the water reservoir 270, as water is pushed out of the reservoir 270 through the lens wash tubing 245c, the air pump 215 replaces lost air supply in the reservoir 270 to maintain a substantially constant pressure, which in turn provides for a substantially constant lens wash flow rate. In some embodiments, a filter (not shown) may be placed in the path of the gas supply tubing 240c to filter-out undesired contaminants or particulates from passing into the water reservoir 270. In some embodiments, outflow check valves or other 1-way valve configurations (not shown) may be placed in the path of the lens wash supply tubing to help prevent water from back-flowing into the reservoir 270 after the water has passed the valve.

A relatively higher flow rate compared to lens wash is typically required for irrigation water, since a primary use is to clear the treatment area in the patient of debris that obstructs the user's field of view. Irrigation is typically achieved with the use of a pump (e.g., peristaltic pump), as described. In embodiments with an independent water source for irrigation, tubing placed in the bottom of a water source is passed through the top of the water source and threaded through the head on the upstream side of the pump. Tubing on the downstream side of the pump 255c is connected to the irrigation feed line 255b in the umbilical 260 and the irrigation supply line 255a endoscope 100 via the irrigation connection 293 on the connector portion 265. When irrigation water is required, fluid is pumped from the water source by operating the irrigation pump, such as by depressing a footswitch (not shown), and flows through the irrigation connection 293, through the irrigation feed line 255b in the umbilical, and down the irrigation supply line in the shaft 100a of the endoscope to the distal tip 100c. In order to equalize the pressure in the water source as water is pumped out of the irrigation supply tubing, an air vent (not shown) may be included in the top (e.g., a cap or enclosure) 280 of the water reservoir 270. The vent allows atmospheric air into the water source preventing negative pressure build-up in the water source, which could create a vacuum that suctions undesired matter from the patient back through the endoscope toward the water source. In some embodiments, outflow check valves or other 1-way valve configurations (not shown), similar to the lens wash tubing 245c, may be placed in the path of the irrigation supply tubing to help prevent back-flow into the reservoir after water has passed the valve.

Figure 3:
FIG. 3 illustrates various aspects of a tubing assembly for an endoscopic system according to the present disclosure.

FIG. 3 illustrates various aspects of a tubing assembly for an endoscopic system according to the present disclosure. As shown in FIG. 3, a tubing assembly 500 may include an enclosure system 502 that includes a cap 510 coupled to a tubing assembly 501. In some embodiments, tubing assembly 501 may be integrated into cap 510. In various embodiments, cap 510 may be configured as a multi-threaded cap capable of attaching to numerous types of fluid containers (e.g., sterile irrigation bottles) with minimal or even no configurations required. Tubing assembly 501 may include a plurality of tubing, such as a gas supply tubing, lens wash supply tubing, and/or irrigation supply tubing.

Accordingly, in some embodiments, cap 510 may include all possible connections (e.g., water, air, CO2, irrigation, insufflation, and/or the like) used during a procedure as well as multi-threaded device(s) to accommodate the variance in characteristics of fluid containers (e.g., neck characteristics, thread characteristics, and/or the like). Cap 510 may include multiple connection ports (see, for example, FIGS. 4A-4C) in order to include multiple options into one irrigation cap -tube assembly (an extra boss may be required for a CO2 connection option). Cap 510 may be designed to include or interface with configurations for specific scope processors and other functions, for example, to accommodate a large and small peristaltic options.

Figure 4A:
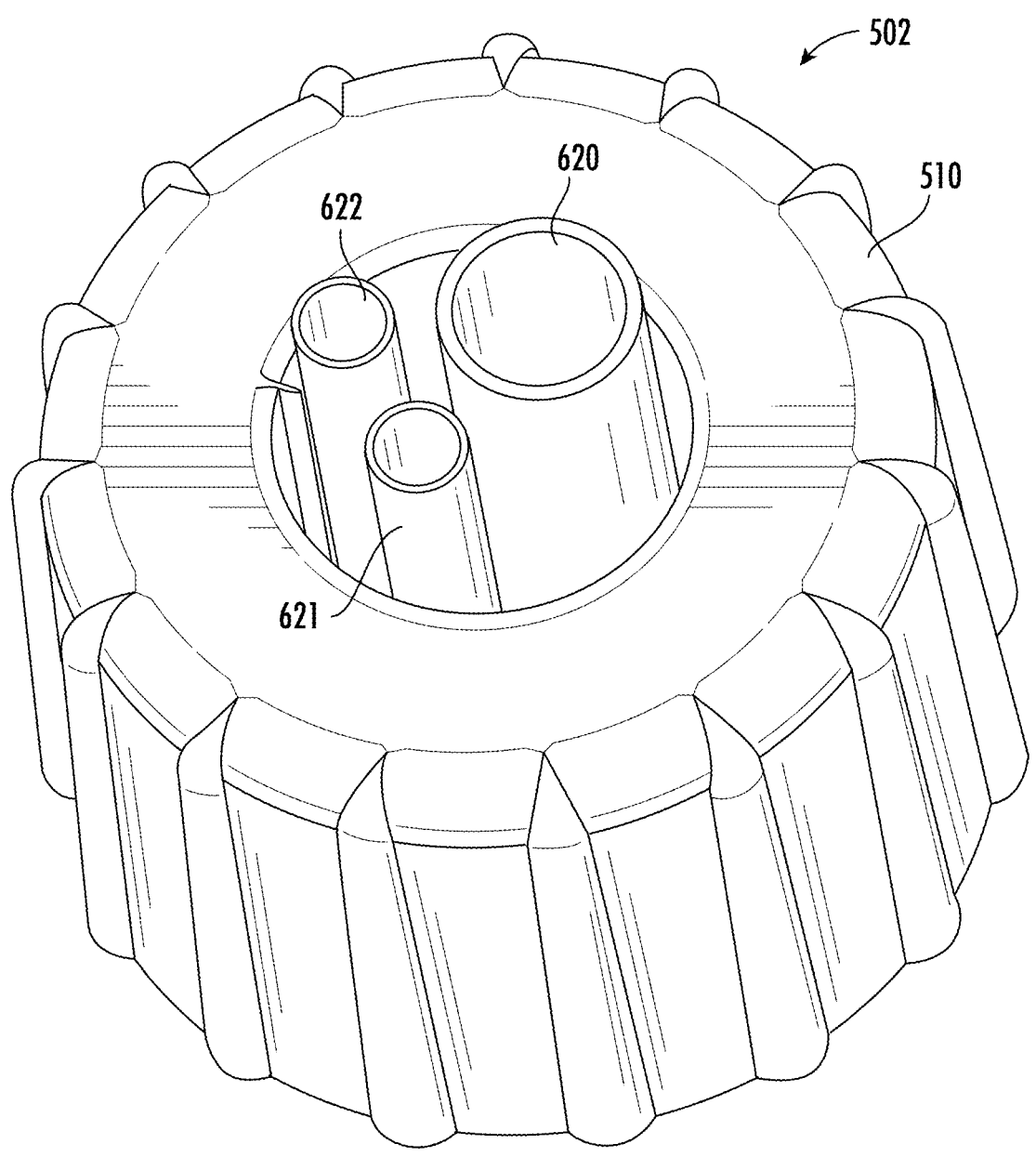
FIG. 4A illustrates a top perspective view depicting various aspects of an enclosure system according to the present disclosure.
Figure 4B:
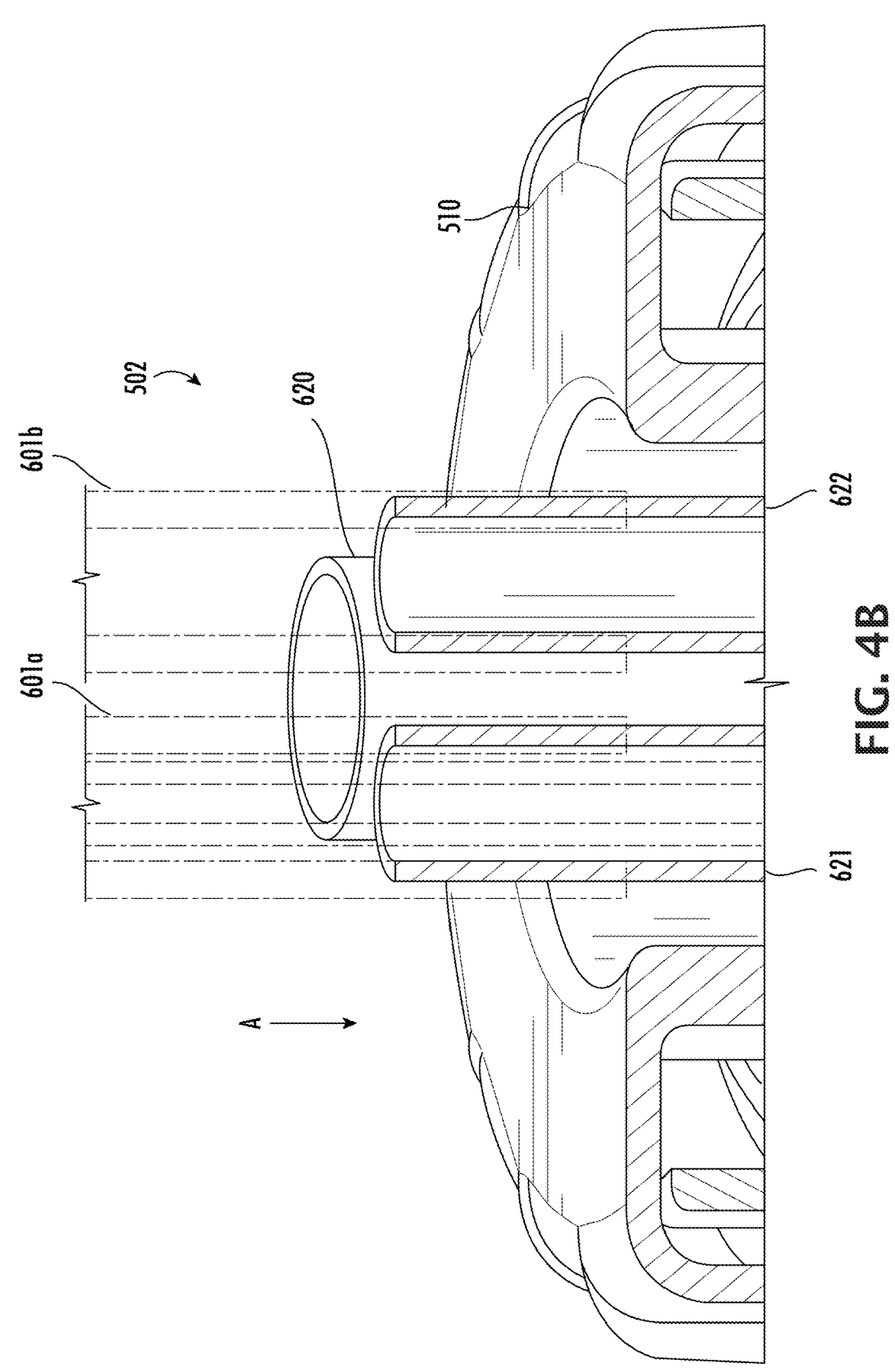
FIG. 4B illustrates a partial side sectional view depicting various aspects of an external-coupling embodiment of the enclosure system of FIG. 4A.
Figure 4C:
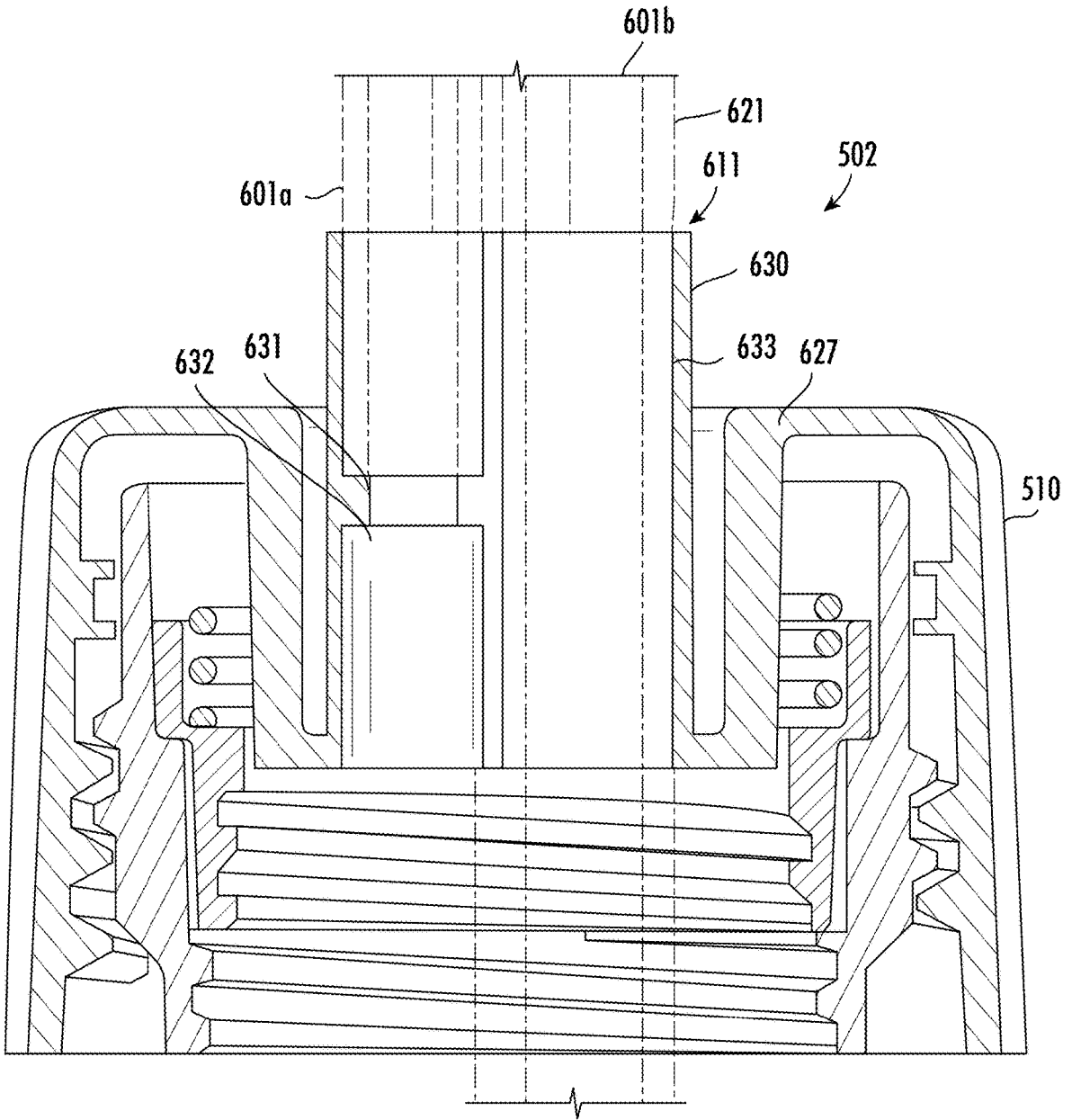
FIG. 4C illustrates a side sectional view depicting various aspects of an internal-coupling embodiment of the enclosure system of FIG. 4A.

In various embodiments, tubing 501 may be coupled to tubing 505 via ports in cap 510 (see, for example, FIGS. 4A-4C). Tubing 505 may be coupled to an endoscope, for example, via air/water channel 503 and/or gas channel 504. Tubing 505 may be configured as a disposable tubing kit for one-time use during an endoscopic procedure.

At least a portion of tubing 501 may be arranged within a fluid container coupled to cap 510 during the endoscopic procedure. Tubing 501 may be configured the same or substantially similar to tubing 240c, 245c, and/or 255c described in the present disclosure. In some embodiments, tubing 501 may include a large irrigation tubing 507, for example, to facilitate peristaltic irrigation functions.

FIG. 4A illustrates a top perspective view depicting various aspects of an enclosure system according to the present disclosure. As shown in FIG. 4A, enclosure system 502 may include a cap 510 having ports 620-622. In various embodiments, ports 620 may be used to connect tubing for various functions, such as air, water, CO2, irrigation, insufflation, scope-specific processor connections, and/or the like. For example, port 620 may be configured as an irrigation connection, for instance, for a large irrigation tube designed for peristaltic irrigation. Port 621 may be for scope-specific processor connections and port 622 may be configured to receive a CO2 insufflation tube. In various embodiments, external tubing (i.e., tubing that is not port of cap 510, for instance tubing 502) may be connected or bonded to cap 510 via ports through external bonding or internal bonding (see, for example, FIGS. 4B and 4C, respectively).

Although a large irrigation port, a CO2 port, and a scope-specific processor connections port are used in the example depicted in FIG. 4A, embodiments are not so limited, as enclosure systems may include more or less ports configured to interface with different functions in accordance with the present disclosure.

FIG. 4B illustrates a partial side sectional view depicting various aspects of an external-coupling embodiment of the enclosure system of FIG. 4A. In an external-coupling embodiment, external tubing sets 601a, 601b may be coupled or bonded to cap 510 by pressing tubing 601a, 601b over corresponding ports or nipples 620-622 protruding from cap 510 to force tubing 601a, 601b in direction A toward cap 510. In some embodiments, tubing 601a, 601b may be forced toward cap 510 over ports 620-622 until blocked by an object, such as a surface of cap (e.g., until shouldered against the lowest point possible on an upper surface of cap 510). The coupling or bonding occurs between an internal surface or diameter of tubing 601a, 601b and an external surface or diameter of corresponding ports 620-622.

FIG. 4C illustrates a side sectional view depicting various aspects of an internal-coupling embodiment of the enclosure system of FIG. 4A. In some embodiments, tubing sets 601a, 601b, may be coupled or bonded to cap 510 internally, for example, to support pressurized operation. Internal-coupling may include a vertical-wall coupling embodiment and/or a shoulder coupling embodiment. In a vertical-wall coupling embodiment, tubing 601b extends through an opening 611 in cap 510, for example, through a port cavity, lumen, or other structure 627, and the external wall 621 of tubing 601b engages an internal surface 633 of cap 510 to couple or bond tubing 601b to cap 510. Accordingly, tubing may pass through cap 510 and bond to the vertical walls of the cap 510. In a shoulder-coupling embodiment, tubing 601a may pass through opening 611 and be forced over port 631 until tubing 601a contacts shoulder 632 of port 631. A coupling or bond may occur between tubing 601a and vertical wall 633, outer walls of port 631, and/or upper surface of shoulder 632.

Figure 5:
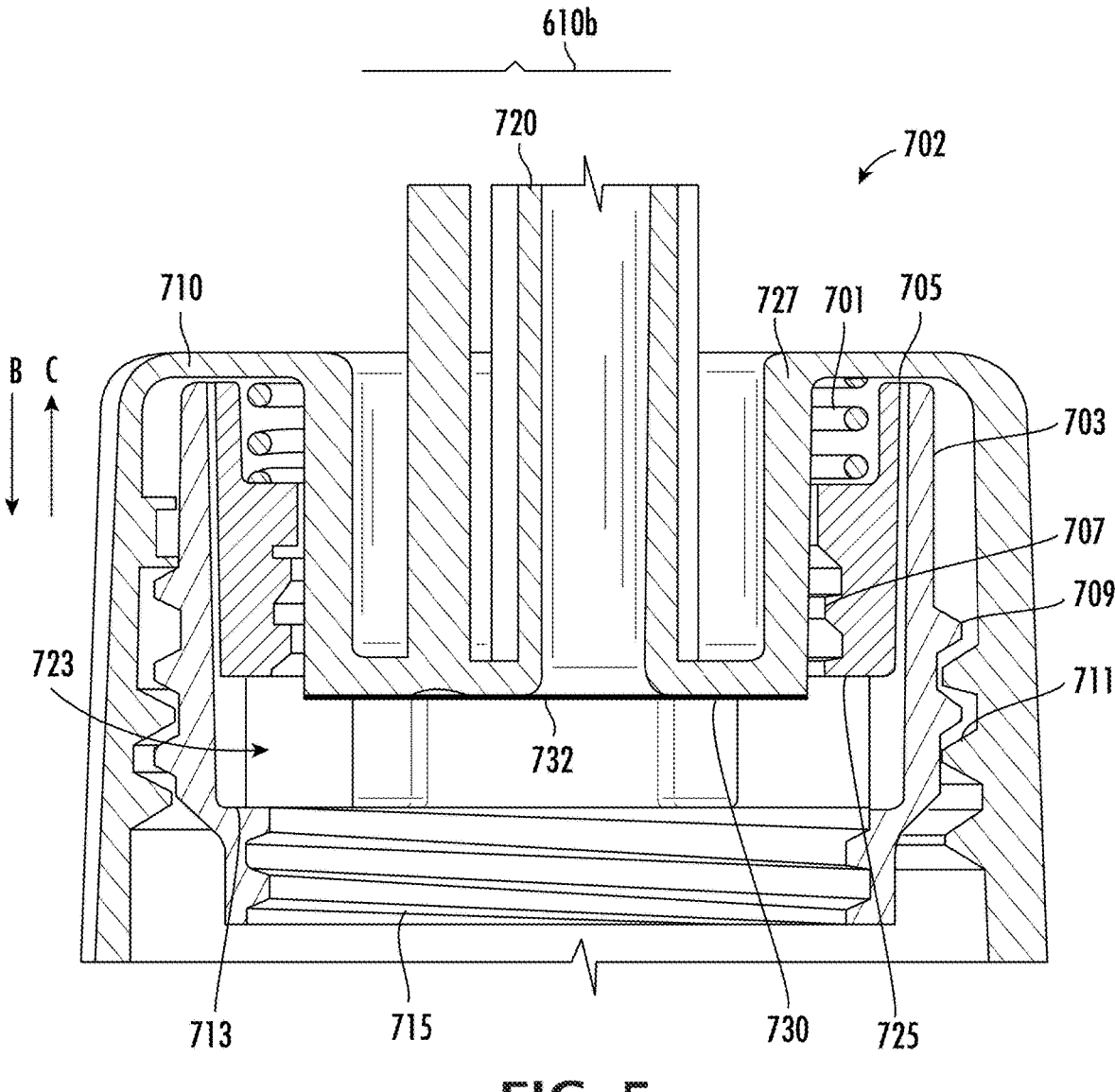
FIG. 5 illustrates a side sectional view depicting various aspects of an enclosure system according to the present disclosure.

FIG. 5 illustrates a side sectional view depicting various aspects of an enclosure system according to the present disclosure. As shown in FIG. 5, an enclosure system 702 may include a cap 710 configured to be installed on a port (e.g., a neck) of a fluid container, such as fluid container 270 of the present disclosure. In some embodiments, cap 710 may include a plurality of modules, carriers, carriages, or other interface elements arranged within an internal cavity of cap 710 (e.g., an interior space formed within cap 710) that may be configured to engage fluid container ports of different characteristics, including different thread configurations (for instance, size, OD, pitch, spacing, and/or the like) and/or different port dimensions (for instance, OD).

In various embodiments, cap 710 may include a primary (large-dimension or carrier ring) carriage 703 arranged within the internal cavity of cap 710 and configured to engage larger dimensioned fluid container ports and a secondary (small-dimension or floating ring) carriage 705 that may be arranged within an internal cavity of primary carriage 703 (e.g., an inner space arranged within primary carriage 703; "internal primary cavity") to engage smaller dimensioned fluid container ports. In some embodiments, larger/smaller dimensions may be or may include OD port, OD thread, and/or the like.

In some embodiments, the dimension difference between primary carriage 703 and secondary carriage 705 may be about 0.25 mm, about 0.5 mm, about 1 mm, about 1.25 mm, about 1.5 mm, about 2 mm, about 2.5 mm, about 3 mm, about 3.5 mm, about 4 mm, about 5 mm, about 10 mm, about 20 mm, about 30 mm, and any value or range between any two of these values (including endpoints). In some embodiments, the dimension difference between primary carriage 703 and secondary carriage 705 may be about 2.55 mm (difference in thread outer diameter outside of United States (US) (OUS)), about 3.06 mm (difference in OUS-US OD thread), and any value or range between any two of these values (including endpoints) (see, for example, Table 1, below).

Primary carriage 703 may include external threads 709 configured to engage threads 711 of cap 710, for example, to couple primary carriage 703 to cap 710. In some embodiments, primary carriage 703 may be rotated within cap to move in one of directions B and C via the engagement between threads 709 and 711. In various embodiments, primary carriage 703 may include internal threads 715 (e.g., primary internal threads) configured to engage corresponding threads on a fluid container port (not shown; see, for example, FIGS. 7D-7G).

Secondary carriage 705 may include internal threads 707 (e.g., secondary internal threads) configured to engage corresponding threads on a fluid container port (i.e., smaller thread OD than for primary carriage 703). In some embodiments, secondary carriage 705 may be biased in direction B by a spring (or other biasing member) 701 arranged within cap 710. Accordingly, in the absence of a force on secondary carriage 705 in direction C, secondary carriage 705 may be arranged within space 723, for example, with a lower surface 725 of secondary carriage 705 resting against shoulder 713 of primary carriage 703. In some embodiments, spring 701 may operate to control rebound of secondary carriage 705 out of (or down (i.e., direction B) through) primary carriage 703 for fluid container ports that require secondary carriage 705 to move for installing a fluid container port in cap 710 and/or sealing via sealing element 730.

In various embodiments, one or more sealing elements may be arranged within cap 710 to form a seal with fluid container ports installed within cap. For example, a sealing element or surface 730, such as an o-ring, washer, or a layer of sealing material, may be arranged on/about or coupled to internal surface 732, for example, a bottom surface of port cavity 727. In this manner, when a fluid container port is installed within cap, an upper surface of the port may form a seal (e.g., a compression seal) with sealing element 730. In some embodiments, sealing element 730 may be formed of various materials, such as a polymer, silicone, a thermoplastic elastomer, variations thereof, combinations thereof, and/ or the like.

Figure 7A:
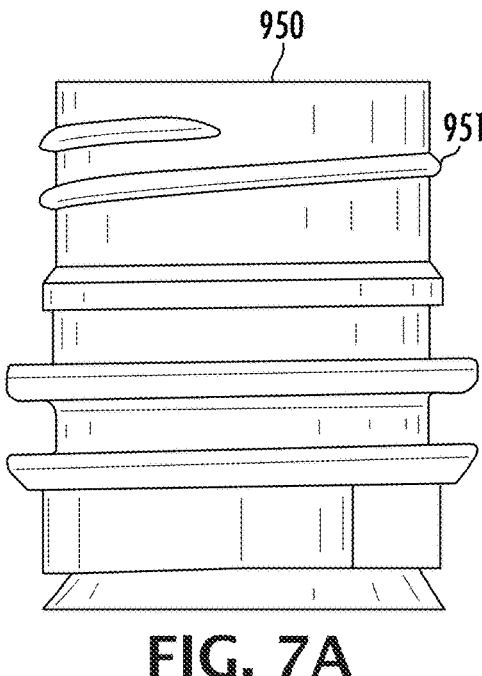
FIGS. 7A-7C illustrates various aspects of example fluid container ports that may be installed within enclosure systems according to the present disclosure.
Figure 7B:
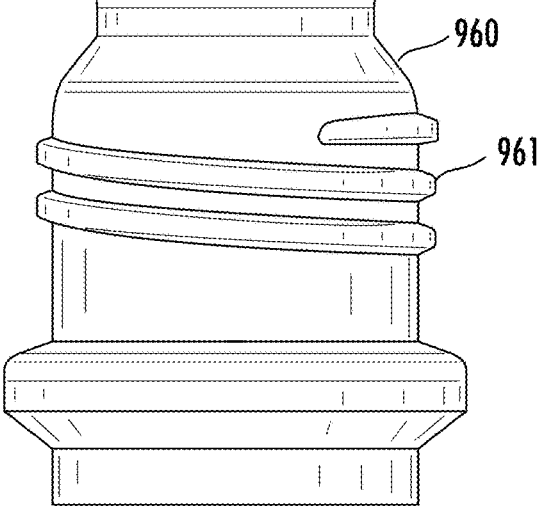
Figure 7C:
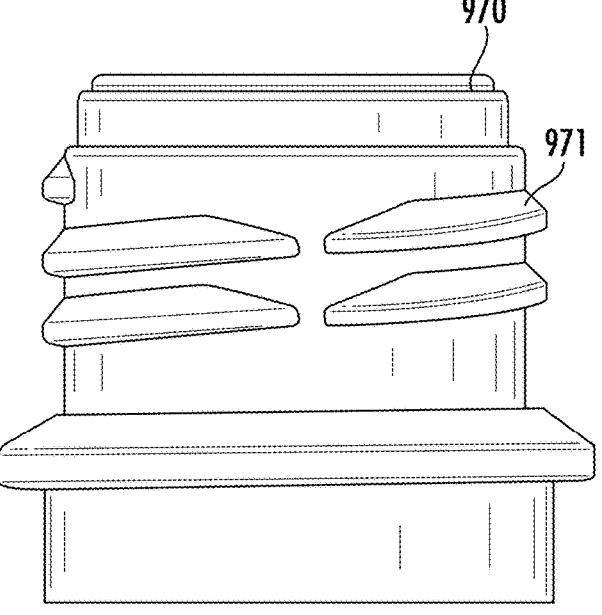
Figure 7D:
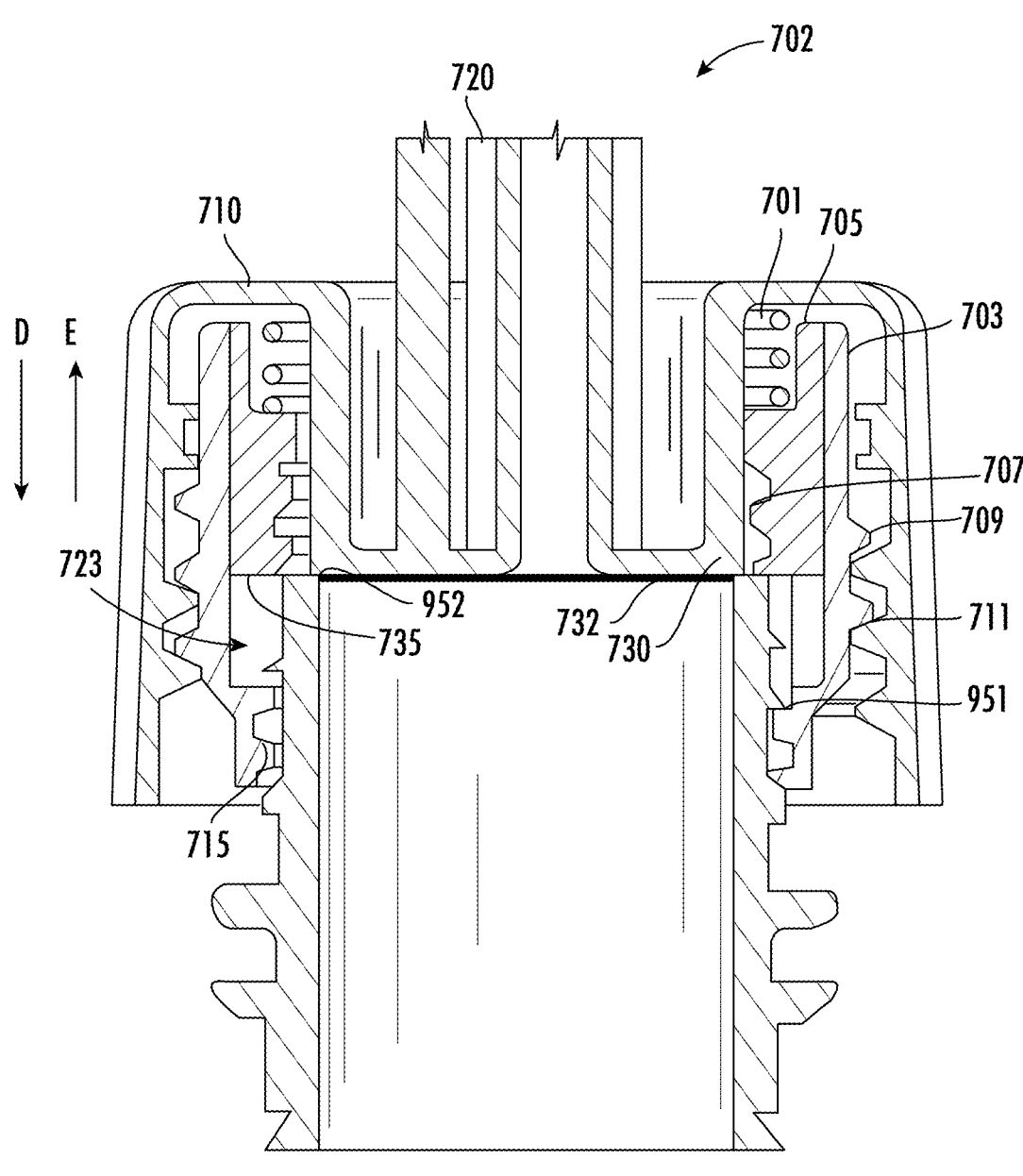
FIGS. 7D-7G illustrates various aspects of enclosure systems installed on example fluid container ports that may be installed within enclosure systems according to the present disclosure.

In general, secondary carriage 705 may be configured for smaller OD thread connections (see, for example, FIG. 7F) and may translate out of the larger OD ports and OD threads (see, for example, FIG. 7D). In various embodiments, primary carriage 703 may be threaded via threads 709 so that when secondary carriage 705 reaches the extent of its translation and the fluid container port requires more room to reach sealing surface 730, primary carriage threads 709 allow primary carriage 703 to ride up (i.e., direction C) into cap 710 (see, for example, FIG. 7D).

In some embodiments, a torque control element (not shown) may be used to control the torque required for primary carriage 703 to thread into and out of cap 710. In some embodiments, the torque control element may include an o-ring gland and/or o-ring to control the threading torque of primary carriage 703 within cap 710. For example, an o-ring may be arranged above threaded sections (for example, 707, 709, and/or 711) and below the internal ceiling of cap 710, for instance, to provide interference or resistance to rotation for primary carriage 703.

Figure 6A:
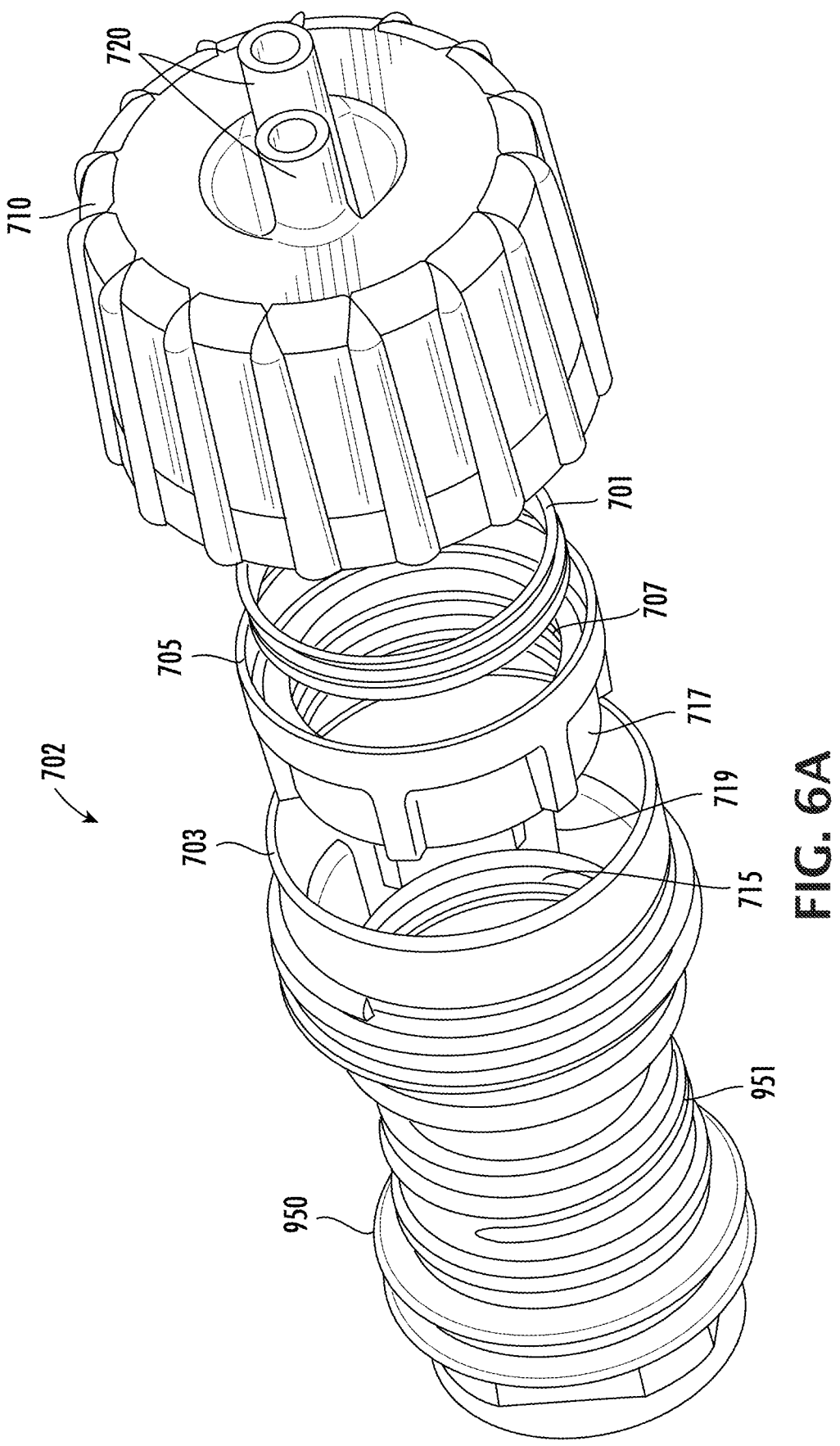
FIG. 6A illustrates an exploded perspective view depicting various aspects of an enclosure system with fluid container port according to the present disclosure.
Figure 6B:
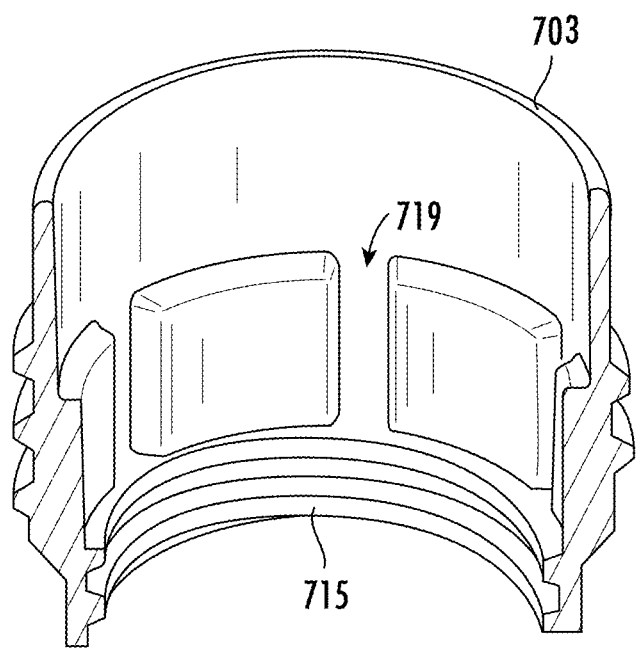
FIG. 6B illustrates a side sectional view depicting various aspects of a primary carriage element of the enclosure system of FIG. 6A.
Figure 6C:
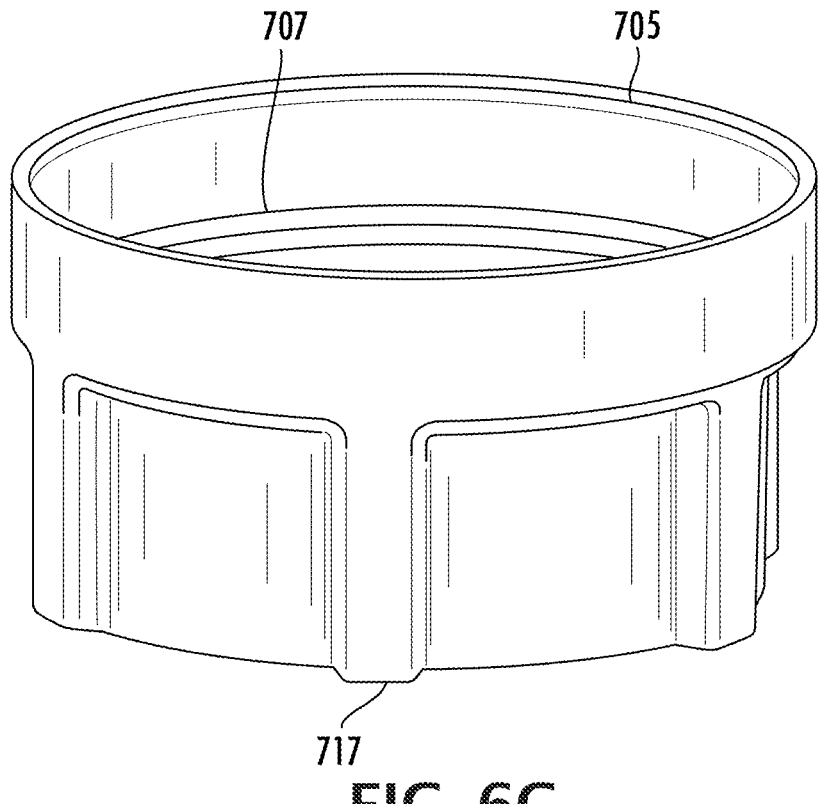
FIG. 6C illustrates a side perspective view depicting various aspects of a secondary carriage element of the enclosure system of FIG. 6A.

FIG. 6A illustrates an exploded perspective view depicting various aspects of an enclosure system with fluid container port according to the present disclosure. Enclosure system 702 may be configured to receive a fluid container port 950 having threads 951 (see for example, FIGS. 7A and 7D). As shown in FIG. 6A, one or more guide protrusions, ridges, or bosses 717 may be arranged on an outer surface of secondary carriage 705. Guide bosses 717 may be configured to be seated or otherwise arranged within corresponding guide cavities or slots 719 within primary carriage 703. FIG. 6B illustrates a side sectional view depicting various aspects of a primary carriage element of the enclosure system of FIG. 6A showing, among other things, guide slots 719 within primary carriage 703. FIG. 6C illustrates a side perspective view depicting various aspects of a secondary carriage element of the enclosure system of FIG. 6A showing, among other things, guide bosses 717 arranged around the outside of secondary carriage 705. Guide bosses 717 may engage guide slots 719 to prevent rotational movement (i.e., spinning) of primary carriage 703 and/or secondary carriage 705 within cap 710. In this manner, rotation of cap 710 may occur (for example, to thread cap 710 further down on primary carriage 703) without causing corresponding rotation of primary carriage 703 and/or secondary carriage 705, which would prevent threading of cap 710 in direction B (toward fluid container).

FIGS. 7A-7C illustrates various aspects of example fluid container ports that may be installed within a single enclosure system according to the present disclosure. FIG. 7A depicts port 950 (i.e., a neck of a fluid container) with threads 951, FIG. 7B depicts port 960 with threads 961, and FIG. 7C depicts port 970 with threads 971, each with dimensions as indicated in Table 1:

TABLE 1

| Bottle | Thread Pitch (mm) | OD Port (mm) | OD Thread (mm) | Thread Width (mm) |
|---|---|---|---|---|
| 950 | 4.00 | 32.2-32.9 | 35.75 | 2.40 |
| 960 | 3.94 | 30.40 | 33.20 | 2.66 |
| 970 | 4.25 (4.23 IN CAD = 6TPI) | 33.60 | 36.26 | 1.83 |

Δ OD Thread OUS 2.55 mm (950-960)
Δ OD Thread OUS-US 3.06 mm (970-950)

Although bottles 950, 960, and 970 having dimensions specified in Table 1 are used in some examples in the present disclosure, embodiments are not so limited, as enclosure systems may be configured to accommodate a plurality of fluid container ports with different dimensions depending on the particular design and configuration of the enclosure system and components thereof.

FIGS. 7D-7G illustrates various aspects of enclosure systems installed on example fluid container ports that may be installed within enclosure systems according to the present disclosure. Referring to FIG. 7D, therein is depicted port 950 installed within cap 710. Port 950 is a larger-dimensioned port; accordingly, port 950 is installed within primary carriage 703. To install cap 710 on port 950, cap 710 may be pushed down onto port 950 in direction D until threads 715 contact threads 951, preventing further movement of cap 710 in direction D. At this stage, port 950 may be threaded into cap 710 via engagement of threads 715 and threads 951, causing movement of cap 710 down port 950 in direction D (and port 950 up into cap 710 in direction E). As port 950 moves up into cap 710, an upper surface 952 of port 950 may engage a bottom surface 735 of secondary carriage 705 within space 723, forcing secondary carriage 705 in direction E until upper surface 952 engages sealing element 732, forming a seal between port 950 and cap 710.

Figure 7E:
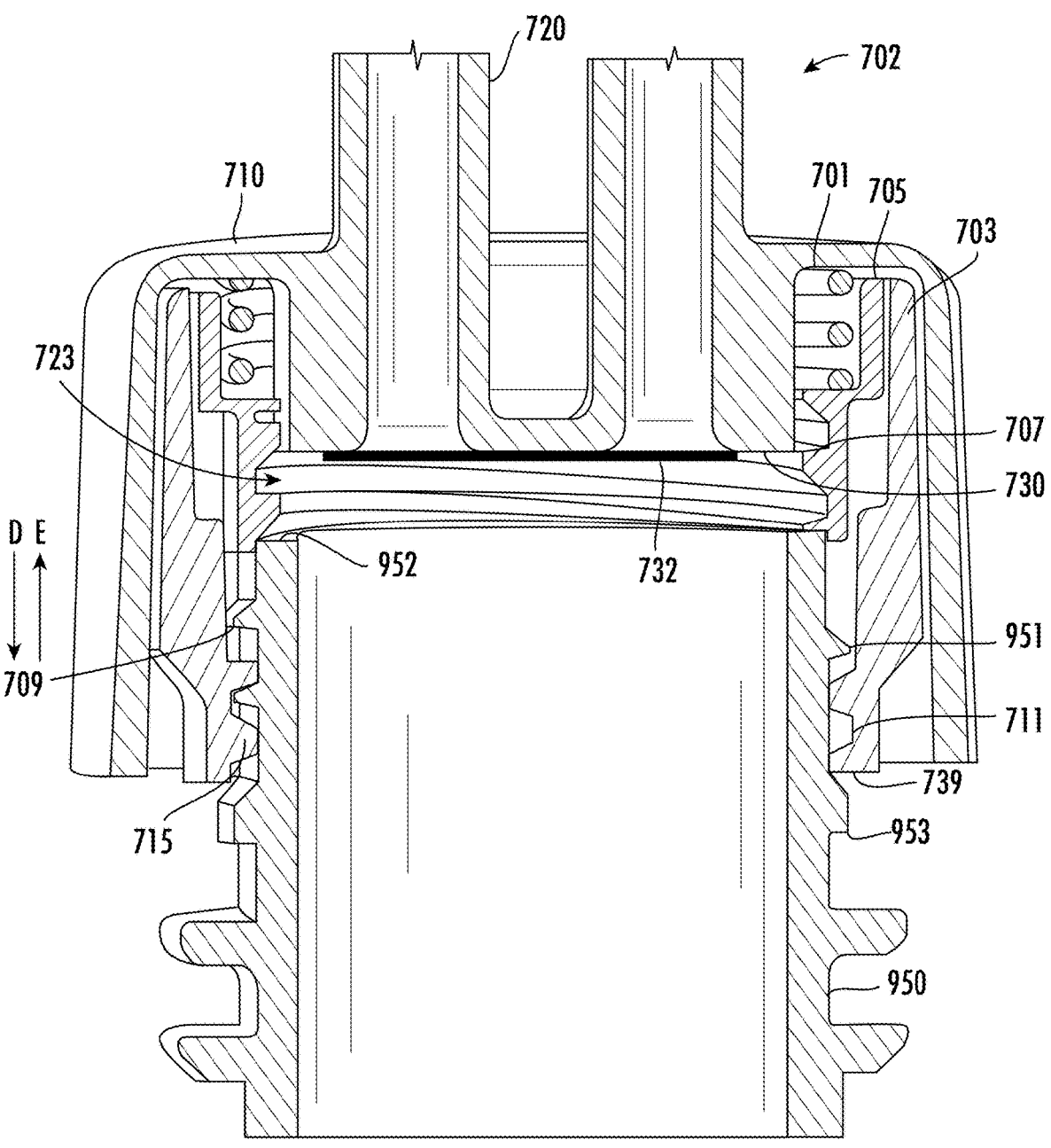

Referring to FIG. 7E, therein is depicted port 950 installed within cap 710. As shown in FIG. 7E, in some configurations of port 950, an interference may arise between flange 953 and a bottom surface 739 of primary carrier that may cause a gap within space 723 between surface 952 and sealing element 732. Accordingly, in some embodiments, threads (not shown) may be incorporated on the inside of cap 710 and externally on primary carrier 703 to allow cap 710 to thread down (i.e., direction E) after flange 953 has made contact with cap 710. Accordingly, in some embodiments, cap 710 may include a set of secondary threads that may allow cap 710 to be threaded down primary carriage 703 after a port (e.g., port 950) has engaged with cap to prevent the port with sealing with sealing element 732, for example, to allow primary the port to engage sealing element 732. For example, referring to FIG. 5, cap 710 may include secondary threads 711 that may engage threads 709 to allow cap 710 to be threaded down primary carriage 703 to reduce or even eliminate any gap between surface 952 and sealing element 732.

Figure 7F:
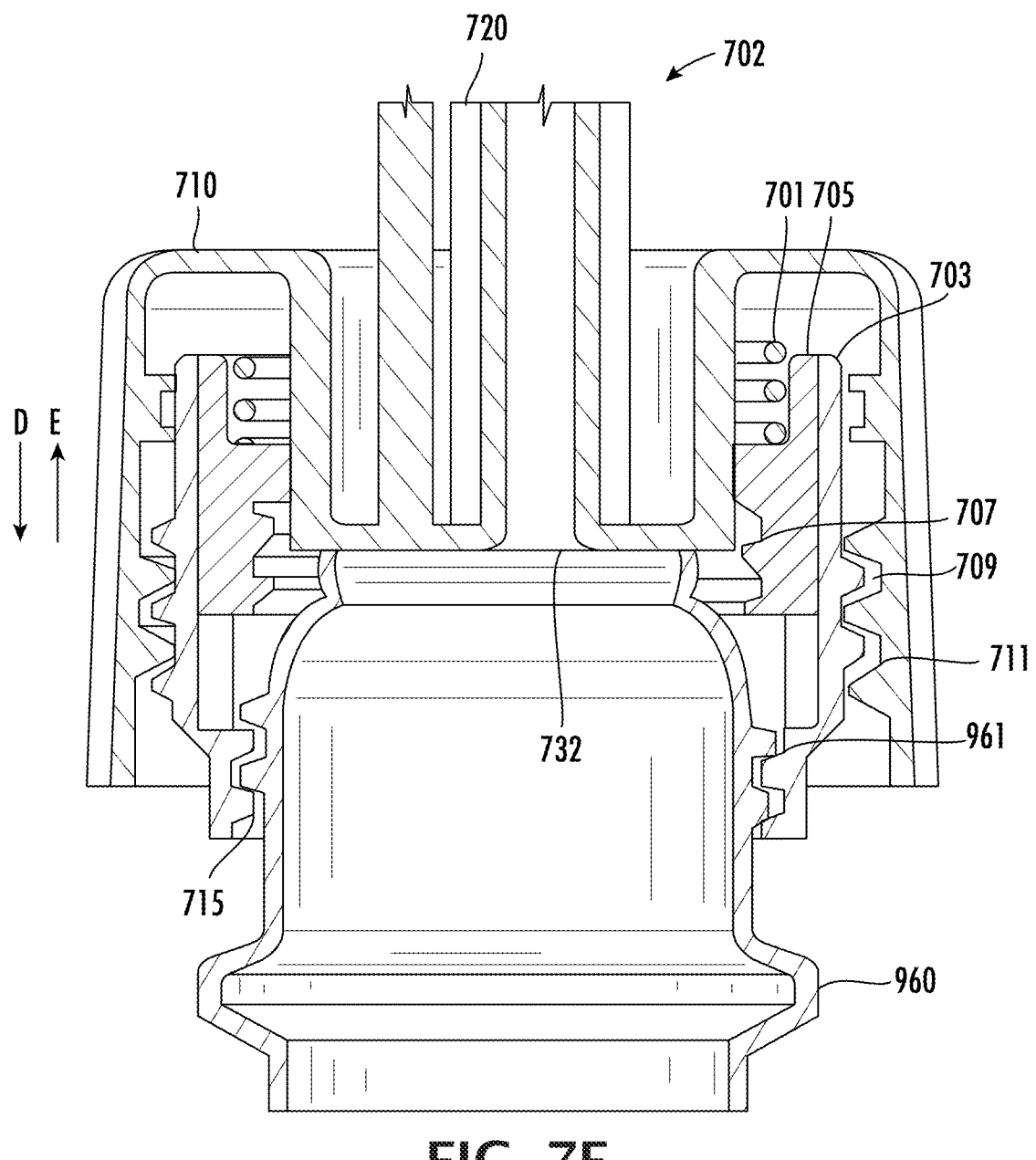

Referring to FIG. 7F, therein is depicted port 960 installed within cap 710. Port 960 is a larger-dimensioned port; accordingly, port 960 is installed within primary carriage 703. To install cap 710 on port 960, cap 710 may be pushed down onto port 950 in direction D until threads 715 contact threads 961, preventing further movement of cap 710 in direction D. At this stage, port 960 may be threaded into cap 710 via engagement of threads 715 and threads 961, causing movement of cap 710 down port 960 in direction D (and port 960 up into cap 710 in direction E), for example, until an upper surface of port 960 engages sealing element 732 (or other internal surface) of cap 710. In some embodiments, a portion of port 960 may engage a portion of secondary carriage 705 while traveling in direction E, pushing secondary carriage 705 up within cap 710.

Figure 7G:
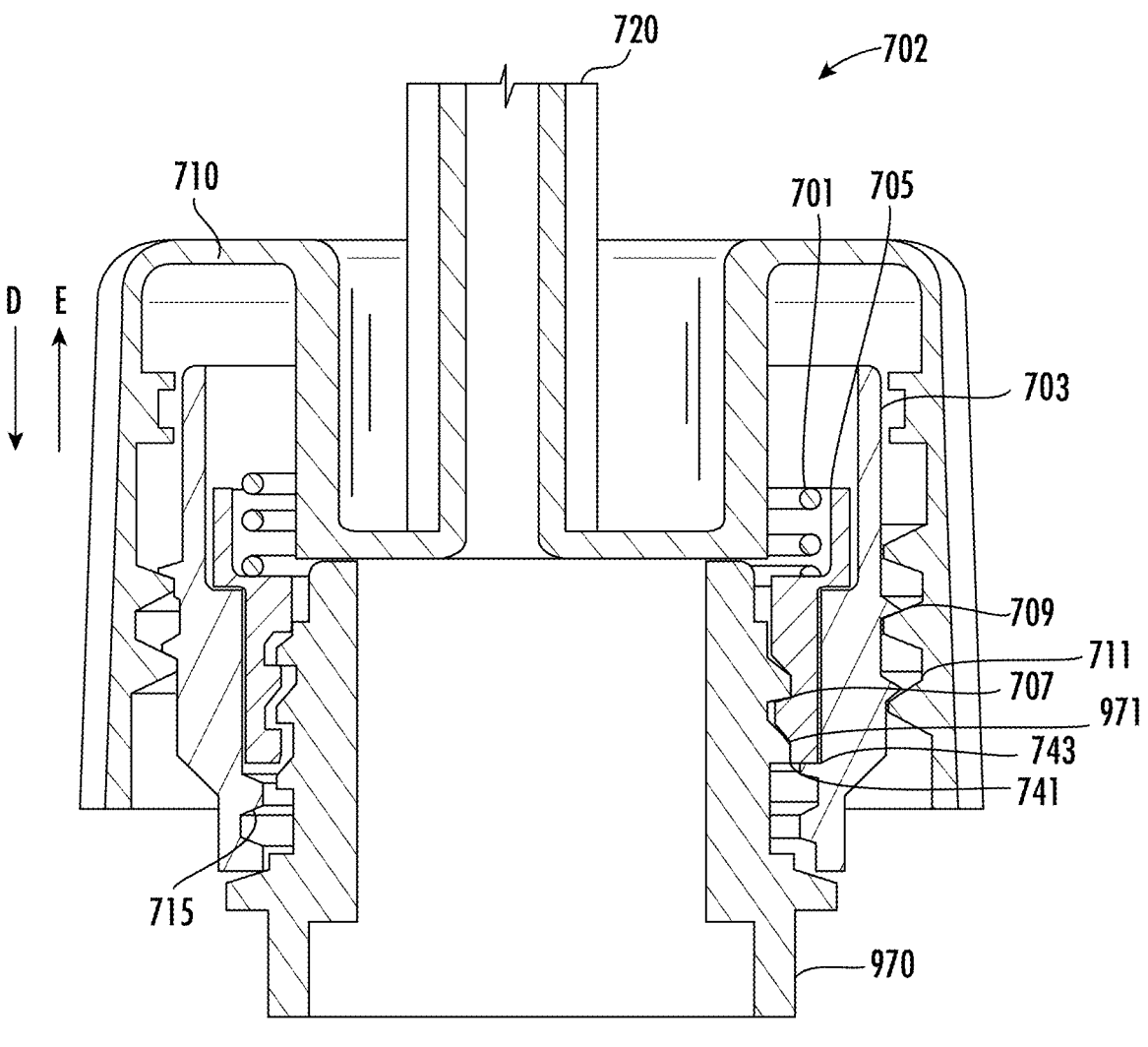

Referring to FIG. 7G, therein is depicted port 970 installed within cap 710. Port 970 is a smaller-dimensioned port; accordingly, port 970 is installed within secondary carriage 705. Prior to installation, secondary carriage 705 is biased in direction D via spring 701 such that bottom surface 741 of secondary carriage 705 is resting against upper surface 743 of primary carriage 703. To install cap 710 on port 970, cap 710 may be pushed down onto port 950 in direction D until threads 707 contact threads 971, preventing further movement of cap 710 in direction D. At this stage, port 970 may be threaded into cap 710 via engagement of threads 707 and threads 971, causing movement of cap 710 down port 970 in direction D (and port 970 up into cap 710 in direction E), for example, until an upper surface of port 970 engages sealing element 732 (or other internal surface) of cap 710.

Figure 8:
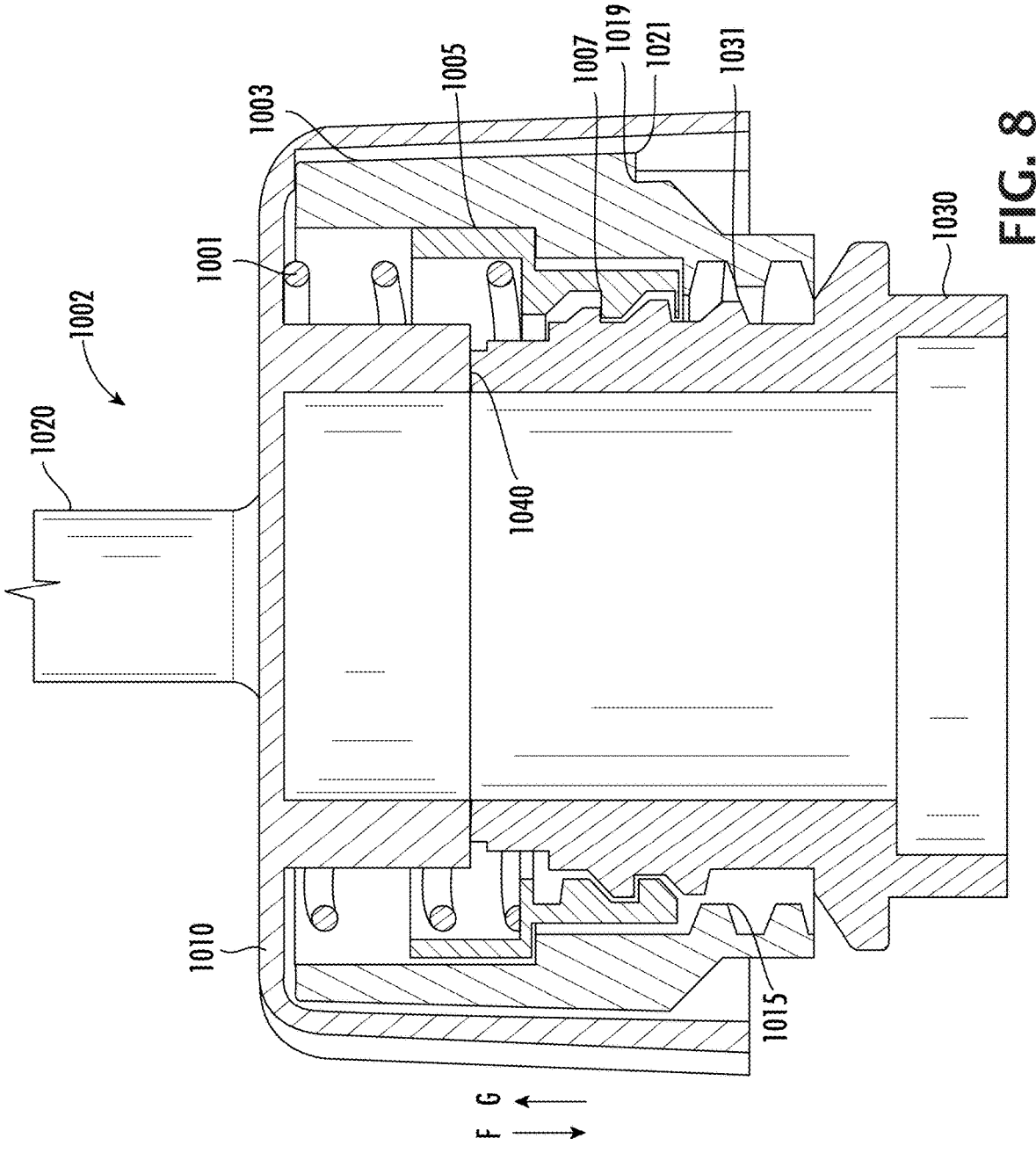
FIG. 8 illustrates a side sectional view depicting various aspects of a clip multi-carriage enclosure system installed on a fluid container port according to the present disclosure.

FIG. 8 illustrates a side sectional view depicting various aspects of a clip multi-carriage enclosure system installed on a fluid container port according to the present disclosure. As shown in FIG. 8, an enclosure system 1002 may include a cap 1010 having at least one port 1020 for connecting tubing (e.g., air, water, CO2) to a fluid container (not shown). In various embodiments, cap 1010 may include a primary (or large-dimension) carriage 1003 configured to engage larger dimensioned fluid container ports and a secondary (or small-dimension) carriage 1005 to engage smaller dimensioned fluid container ports. In some embodiments, primary carriage 1003 and/or secondary carriage 1005 may operate the same or substantially similar to primary carriage 703 and/or secondary carriage 705, respectively.

Primary carriage 1003 may include internal threads 1015 for engaging corresponding threads of larger-dimensioned fluid container ports. Secondary carriage 1005 may include internal threads 1007 for engaging corresponding threads of smaller-dimensioned fluid container ports (e.g., port 1030).

In some embodiments, secondary carriage 1005 is nested inside primary carriage 1003. In various embodiments, primary carriage 1003 may be clipped into outer cap 1010 and may be threaded (via threads 1015) for larger bottle types. Secondary carriage 1005 may be biased by spring (or other biasing member) 1001 and can ride up/down (direction G/direction F) in primary carriage 1003 to float out of the way of large bottle types. Secondary carriage 1005 may be threaded (via threads 1007) for smaller bottle types. The connection between primary carriage 1003 and secondary carriage 1005 may be sprung to prevent free float of the secondary carriage 1005.

Primary carriage 1003 may be snap-fitted into cap 1010. For example, primary carriage 1003 may be installed in cap

1010 by forcing primary carriage up (direction G) into cap 1010 until flange, boss, or other surface 1021 of primary carriage 1003 passes and becomes seated or otherwise engaged with shoulder 1019 of cap 1010. Vertical walls of cap 1010 may flex outward to allow primary carriage 1003 to be pushed up (direction F) into cap until flange 1021 passes shoulder 1019, retaining primary carriage 1003 within cap 1010.

Port 1030 may include threads 1031 configured to engage threads 1007, allowing cap 1010 to be rotated to cause port 1030 to ride up (direction F) within secondary carriage 1005 until port 1030 engages internal surface 1040 of cap 1010 (for example, to form a seal with a sealing element associated with surface 1040).

In some embodiments, spring 1001 may be put into an extended position, pushing secondary carriage 1005 (e.g., operating as a floating ring) down allowing the smaller diameter bottle thread (i.e., 1031) to be readily accepted. Small thread diameter 1031 has clearance through the larger threads (e.g., 1015) in the primary carriage 1003 (e.g., operating as a carrier ring). In various embodiments, primary carriage 1003 may be fixed to the cap (via various methods known to those of skill in the art, such as adhesives, molding, and/or the like), allowing secondary carriage 1005 to move in the up/down (Z direction) axis. Rotating cap 1010 may operate to drive the port and secondary carriage 1005 towards seal 1040 until sufficient contact is made to form an adequate seal (e.g., prevent fluid leakage). The embodiment depicted in FIG. 8 may include guide slots in primary carriage 1003 (not shown, see FIG. 6B) of accepting guide bosses (not shown, see FIG. 6C) on secondary carriage 1005 while preventing rotation of secondary carriage 1005 during cap 1010 attachment.

Figure 9:
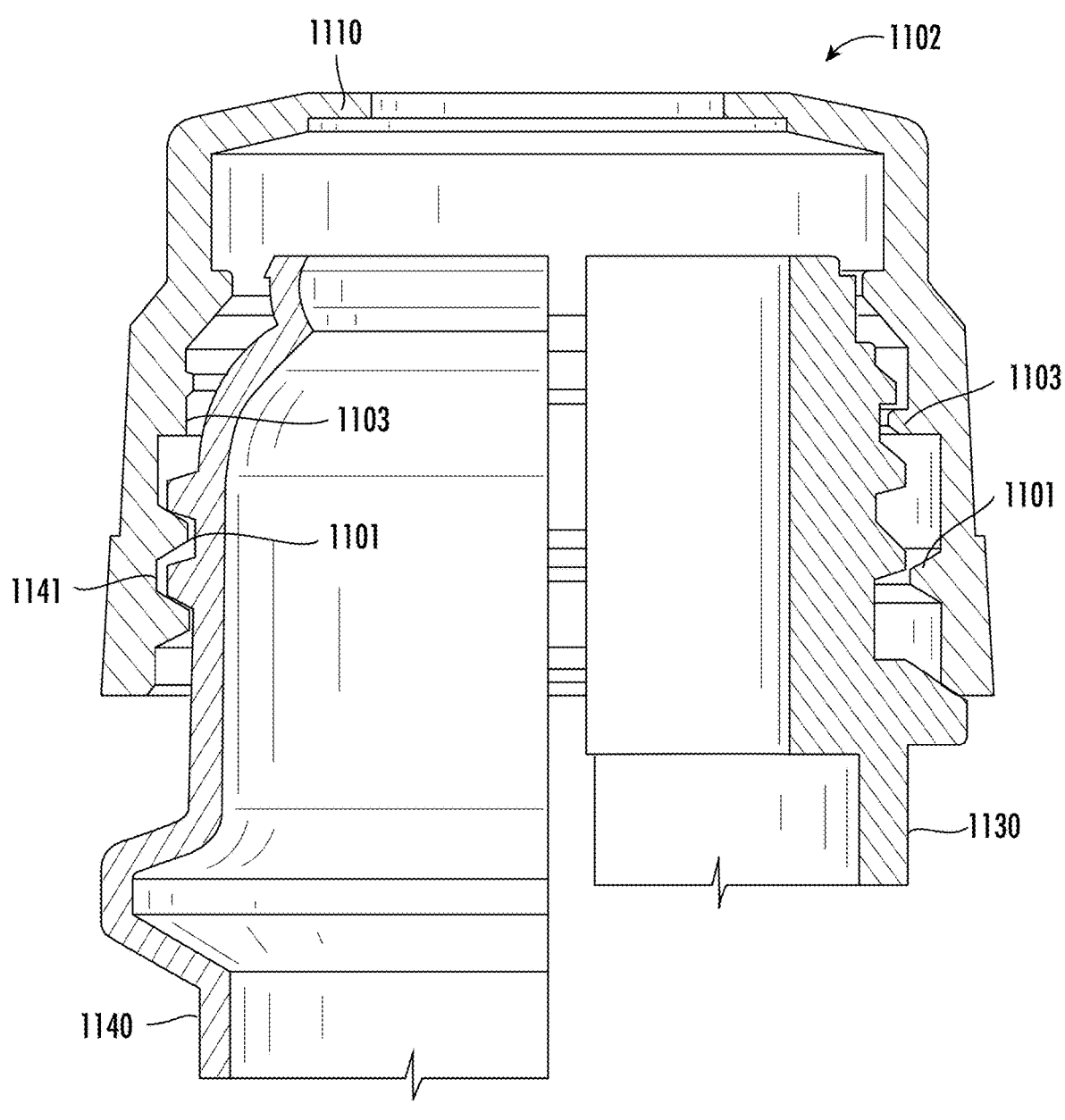
FIG. 9 illustrates a side sectional view depicting various aspects of a stepped thread enclosure system installed on a fluid container port according to the present disclosure.

FIG. 9 illustrates a side sectional view depicting various aspects of a stepped thread enclosure system installed on a fluid container port according to the present disclosure. As shown in FIG. 9, an enclosure system 1102 may include a cap 1110 having a plurality of sets of internal threads configured for different fluid container port configurations. For example, cap 1110 may have threads 1101 for larger-dimensioned ports and threads 1103 for smaller-dimension ports.

For example, port 1140 may be a larger-dimensioned port having threads 1141 (for example, the same or similar to port 960) configured to engage threads 1101. In another example, port 1130 may be a larger-dimensioned port having threads 1131 (for example, the same or similar to port 970) configured to engage threads 1103. In the example depicted in FIG. 9, two (half) ports 1130, 1140 are shown installed within cap 1110. However, this is for illustrated purposes only as only one port (such as one of 1130 or 1140) may be installed within cap 1011 at a time.

To install a port, cap 1110 may be pressed down over the port until one of threads 1101 or 1103 engages corresponding threads of the port (such as 1131 and 1101 or 1141 for 1103). Then, cap 1110 may be rotated to install cap 1110 on the port.

Figure 10:
FIG. 10 illustrates a side perspective view depicting various aspects of a flexible ring enclosure system according to the present disclosure.

FIG. 10 illustrates a side perspective view depicting various aspects of a flexible ring enclosure system according to the present disclosure. As shown in FIG. 10, a cap 1210 may be or may include a flexible component configured as a single, custom, deep, threaded design capable of flexing to allow cap 1210 to flex around the OD port and/or OD thread of the port (not shown) of a fluid container when interference begins to occur as cap 1210 is being pressed down onto the port. Graph 1230 depicts flexible cap 1210 in a deformed condition, depicting forces 1240 and corresponding force information 1242. Graph 1232 depicts flexible cap 1210 in a stressed condition, depicting forces 1240 and corresponding force information 1242.

In some embodiments, internal threads 1201 may be sufficiently deep enough and the material sufficiently flexible enough to allow for sealing forces (e.g., to form a water-tight, gas-tight, hermetic, or other seal) between cap 1210 and port.

In some embodiments, as cap 1210 is pressed down on a port having an OD thread and/or OD port that is larger than am inner diameter (ID) of cap 1210, cap 1210 may flex to increase ID to allow outer threads on port to engage threads 1201. At this stage, cap 1210 may be threaded onto port, with cap 1210 flexing to allow port to ride up through port via engagement of the port threads with threads 1201.

Figure 11:
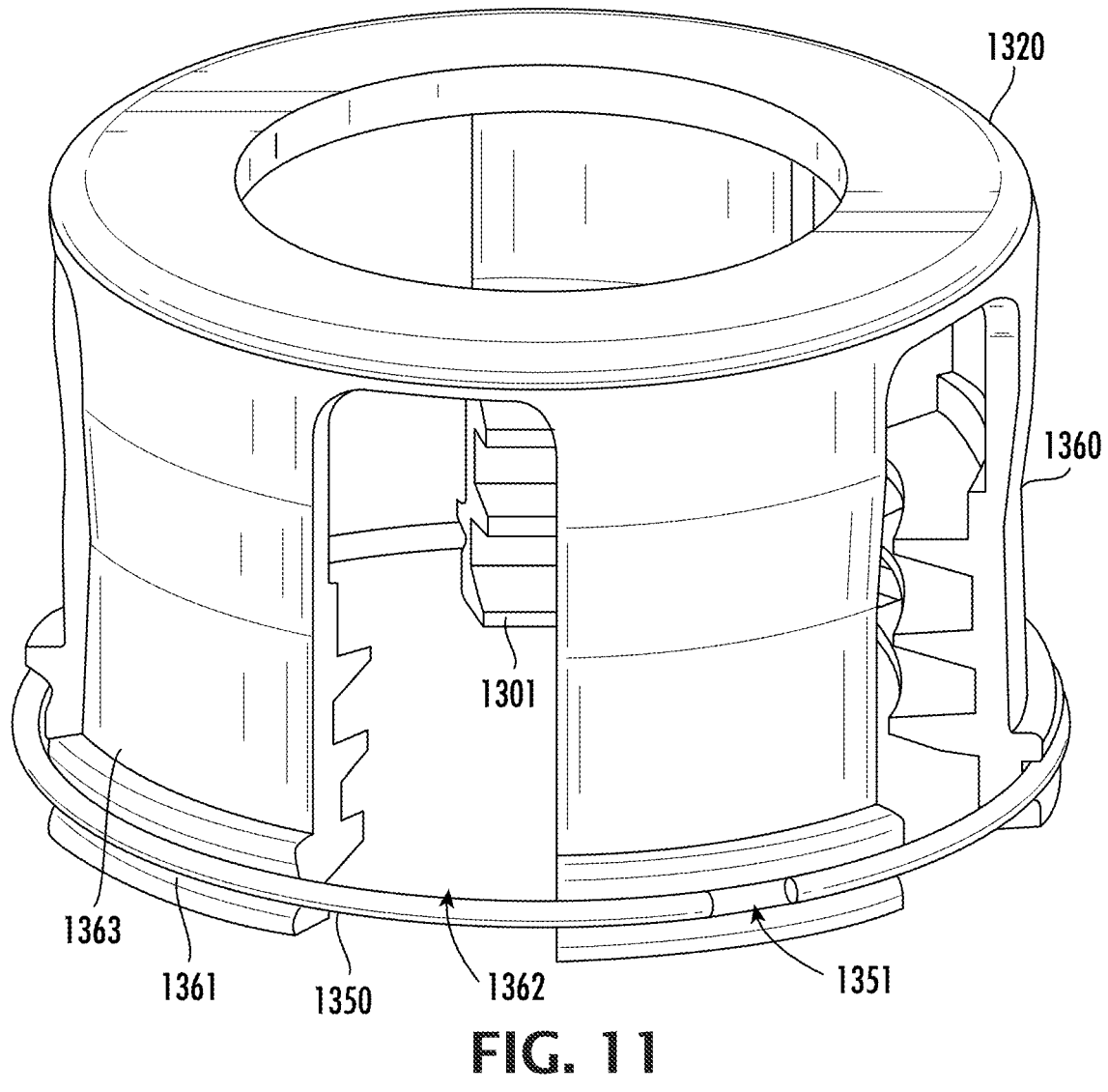
FIG. 11 illustrates a side perspective view depicting various aspects of a slotted ring enclosure system according to the present disclosure.

FIG. 11 illustrates a side perspective view depicting various aspects of a slotted ring enclosure system according to the present disclosure. As shown in FIG. 11, a cap or portion of a cap 1320 may include internal threads 1301 arranged on a skirt 1360 having slots 1362 configured to form legs 1363 in skirt 1360. In some embodiments, component 1320 may be a cap; in other embodiments, component 1320 may be a cap insert (for example, the same or similar to primary carriage 703, secondary carriage 705, insert 1460 of FIG. 10), and/or the like.

Skirt 1360 may be configured to flex radially in an outward direction. In some embodiments, skirt 1360 may be biased to flex outward. Ring 1350 may be arranged around skirt 1360, for instance, held within groove 1361. Ring 1350 may be formed of various rigid materials, such as metal, polymer, variations thereof, combinations thereof, and/or the like. Ring 1350 may be flexible 1351, for instance, due to gap 1351. In some embodiments, ring 1350 may be biased to hold skirt 1360 inward (i.e., against outward bias of skirt 1360).

In some embodiments, as cap 1320 is pressed down on a port having an OD thread and/or OD port that is larger than an ID of skirt 1360, skirt 1360 may flex to increase ID to allow outer threads on port to engage threads 1301. At this stage, cap 1320 may be threaded onto port, with skirt 1360 and ring 1350 flexing to allow port to ride up through port via engagement of the port threads with threads 1201. In some embodiments, ring 1350 may be configured to prevent over-extension of skirt 1360 (for instance, due to forcing cap 1320 on a fluid container port that is too large to be accommodated by cap 1320.

Accordingly, cap 1320 may be configured as a flexible custom, deep, threaded component that allows allowing multiple fluid container port connections.

Figure 12A:
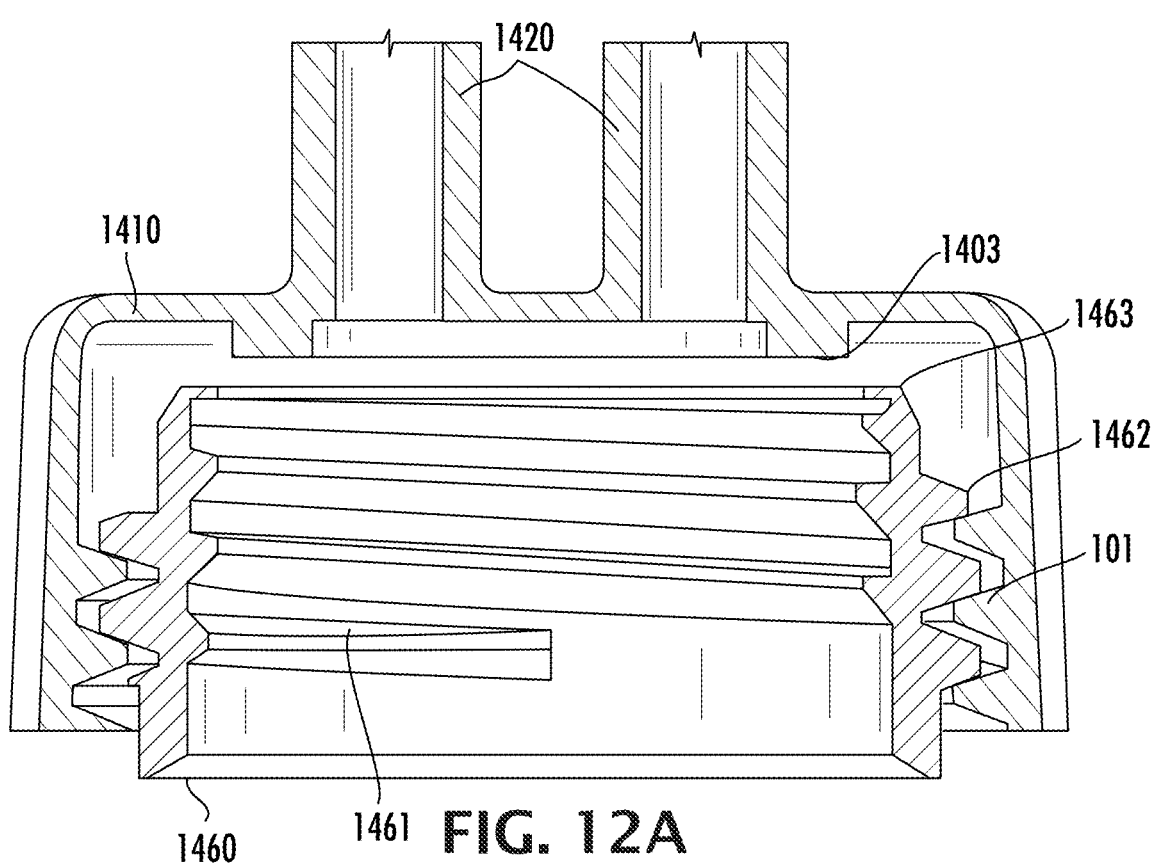
FIG. 12A illustrates a side sectional view depicting various aspects of a dual-threaded insert enclosure system according to the present disclosure.
Figure 12B:
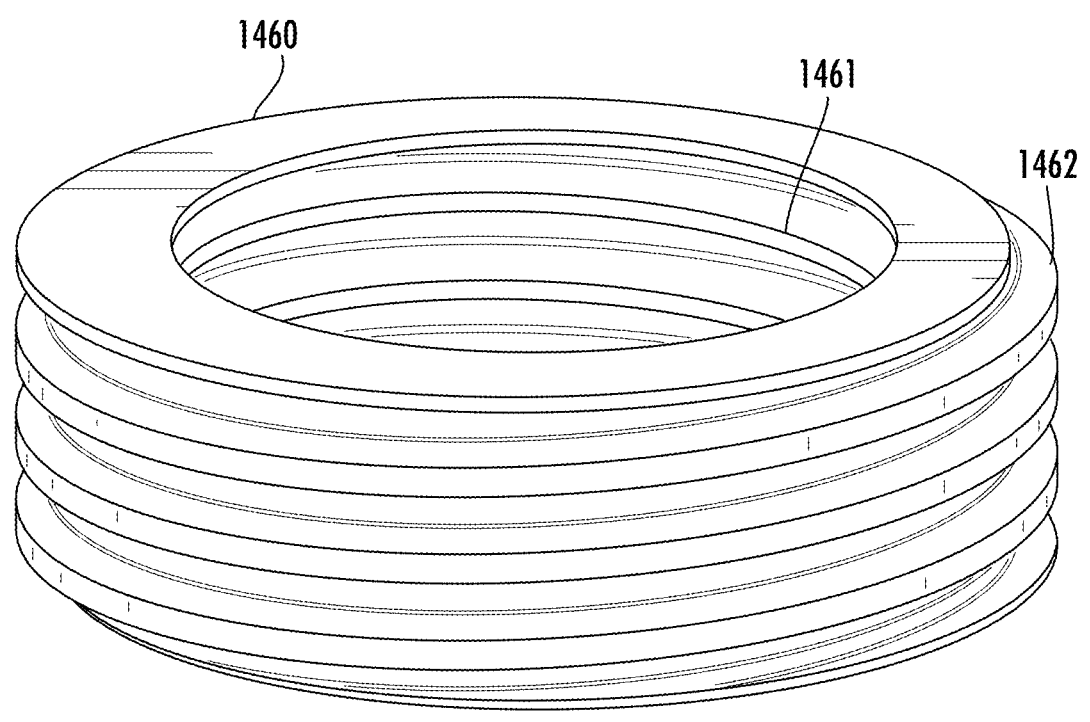
FIG. 12B illustrates a side perspective view of a dual-threaded insert of the enclosure system of 12A.

FIG. 12A illustrates a side sectional view depicting various aspects of a dual-threaded insert enclosure system according to the present disclosure. As shown in FIG. 12A, an enclosure system 1402 may include a cap 1410 having ports 1420 may be configured to receive an insert 1460. Insert 1460 may be dual-threaded, with external threads 1462 configured to engage internal threads 1401 of cap 1410. Internal threads 1461 may be configured to engage corresponding threads of a fluid container port (not shown). FIG. 12B illustrates a side perspective view of dual-threaded insert 1460 depicted in FIG. 12A.

Insert 460 may be threaded up into cap 1410 until upper surface 1463 contacts internal surface 1403. Cap 1410 may be pushed onto a port such that threads 1461 contact corresponding threads of the port, then cap 1410 may be rotated onto port, causing cap 1410 to move down onto port via the engagement between threads 1461 and the port threads. Threads 1462 and 1401 may be threaded (or reversed threaded) such that threading of cap 1410 (via threads 1461) onto the port does not cause insert 1460 to be unthreaded from threads 1401 of cap 1410.

In some embodiments, cap 1410 may receive inserts 1460 of various inner dimensions to accept various types of bottles. For example, cap 1410 may receive inserts with a standard or standard range of OD port, OD threads, and/or other port characteristics so that inserts 1460 may be coupled to cap 1410. The inner dimension (e.g., ID port, ID threads, and/or the like) may be different to accommodate various bottle types. In this manner, a single cap 1410 may be installed on different bottle types through the use of inserts 1460 of differing internal dimensions.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The following claims are hereby incorporated into this Detailed Description by this reference, with each claim standing on its own as a separate embodiment of the present disclosure. Reference signs in the claims are provided merely as a clarifying example and shall not be construed as limiting the scope of the claims in any way.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "the", "first", "second", etc., do not preclude a plurality. Reference signs in the claims are provided merely as a clarifying example and shall not be construed as limiting the scope of the claims in any way.

What is claimed is:

1. An enclosure system for enclosing a plurality of types of fluid containers, comprising:
a cap comprising an internal cavity;
a primary carriage coupled to the cap within the internal cap cavity, the primary carriage comprising a set of primary internal threads configured to engage larger-dimensioned port threads of a larger-dimensioned port of one of the plurality of types of fluid containers; and
a secondary carriage arranged within an internal primary cavity of the primary carriage, the secondary carriage comprising secondary internal threads configured to engage smaller-dimensioned port threads of a smaller-dimensioned port of one of the plurality of types of fluid containers;
wherein the secondary carriage is adjustable relative to the primary carriage in a first configuration and fixed relative to the primary carriage in a second configuration.

2. The enclosure system according to claim 1, further comprising at least one tube of an internal tube set to extend through the cap to access a fluid arranged with the fluid container.

3. The enclosure system according to claim 1, further comprising a spring configured to bias the secondary carriage toward the primary carriage.

4. The enclosure system according to claim 1, further comprising a sealing element arranged on a bottom internal surface of the cap, the sealing element configured to engage a top surface of an installed port to form a seal between the cap and the installed port.

5. The enclosure system according to claim 1, wherein the cap comprises a set of internal cap threads arranged on an inner wall of the internal cavity,
wherein the primary carriage comprises a set of primary external threads configured to engage the internal cap threads to hold the primary carriage within the cap.

6. The enclosure system according to claim 1, wherein the cap comprises a shoulder arranged on an inner wall of the internal cavity,
wherein the primary carriage is configured to be snap-fit via the shoulder to hold the primary carriage within the cap.

7. The enclosure system according to claim 1, a difference in an outer dimension of threads of the larger-dimensioned port and the smaller-dimensioned port being about 2 mm to about 4 mm.

8. The enclosure system according to claim 1, the cap configured to enclose ports having an outer dimension of threads of about 30 mm to about 40 mm.

9. The enclosure system according to claim 1, the primary carriage comprising at least one guiding slot arranged in an internal surface thereof, the secondary carriage comprising at least one guiding boss arranged on an external surface thereof,
the at least one guiding boss configured to be seated within the at least one guiding slot to prevent rotation of the secondary carriage within the cap.

10. An apparatus for performing an endoscopic procedure, comprising:
a fluid container; and
an enclosure system for enclosing the fluid container, the enclosure system configured to be installed on a plurality of types of fluid containers, the enclosure system comprising:
a cap comprising an internal cavity,
a primary carriage coupled to the cap within the internal cap cavity, the primary carriage comprising a set of primary internal threads configured to engage larger-dimensioned port threads of a larger-dimensioned port of one of the plurality of types of fluid containers, and
a secondary carriage arranged within an internal primary cavity of the primary carriage, the secondary carriage comprising secondary internal threads configured to engage smaller-dimensioned port threads of a smaller-dimensioned port of one of the plurality of types of fluid containers;
wherein in a first configuration, the secondary carriage is adjustable relative to the primary carriage.

11. The apparatus according to claim 10, further comprising a spring configured to bias the secondary carriage toward the primary carriage.

12. The apparatus according to claim 10, further comprising a sealing element arranged on a bottom internal surface of the cap, the sealing element configured to engage a top surface of an installed port to form a seal between the cap and the installed port.

13. The apparatus according to claim 10, a difference in an outer dimension of threads of the larger-dimensioned port and the smaller-dimensioned port being about 2 mm to about 4 mm.

14. The apparatus according to claim 10, the cap configured to enclose ports having an outer dimension of threads of about 30 mm to about 40 mm.

\* \* \* \* \*